US010941450B2

(12) United States Patent
Hayashi et al.

(10) Patent No.: US 10,941,450 B2
(45) Date of Patent: Mar. 9, 2021

(54) UROTHELIAL CANCER AND METHODS OF DETECTION AND TARGETED THERAPY

(71) Applicant: THE JOHNS HOPKINS UNIVERSITY, Baltimore, MD (US)

(72) Inventors: Masamichi Hayashi, Baltimore, MD (US); Elisa Guida, Baltimore, MD (US); Mohammad Hoque, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 586 days.

(21) Appl. No.: 15/073,337

(22) Filed: Mar. 17, 2016

(65) Prior Publication Data

US 2016/0273051 A1 Sep. 22, 2016

Related U.S. Application Data

(60) Provisional application No. 62/134,447, filed on Mar. 17, 2015.

(51) Int. Cl.
*C12Q 1/68* (2018.01)
*C12Q 1/6886* (2018.01)
*A61K 31/711* (2006.01)
*A61K 31/7068* (2006.01)

(52) U.S. Cl.
CPC ........ *C12Q 1/6886* (2013.01); *A61K 31/7068* (2013.01); *A61K 31/711* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| 4,882,268 | A | 11/1989 | Penman et al. |
| 5,271,381 | A | 12/1993 | Ailinger et al. |
| 6,017,703 | A | 1/2000 | Kinders et al. |
| 2013/0225662 | A1 | 8/2013 | Kennedy et al. |

FOREIGN PATENT DOCUMENTS

| WO | 2002057787 A2 | 12/2002 | |
| WO | WO-2010099489 A2 * | 9/2010 | ........... C12Q 1/6886 |

OTHER PUBLICATIONS

Olkhov-Mitsel and Bapag. Cancer Medicine 2012; 1(2): 237-260 (Year: 2012).*
The Cancer Genome Atlas Research Network, Nature | vol. 507 | Mar. 20, 2014, pp. 315-322 and Supplementary Information section S7.1 (Year: 2014).*
Ikpatt et al. Laboratory Investigation (Feb. 2010) vol. 90, Suppl. 1, pp. 274A. (Year: 2010).*
Tingting et al. Chinese Journal of Cell Biology. 2013, 35(1): 24-29 (Year: 2013).*
Herman, et al., Methylation-specific PCR: a novel PCR assay for methylation status of CpG islands. Proc Natl Acad Sci U S A. 1996; 93: 9821-9826.
Gitan, et al., Methylation-Specific Oligonucleotide Microarray: A New Potential for High-Throughput Methylation Analysis. Genome Res 2002; 12: 158-164.
Tyagi, et al., Molecular beacons: probes that fluoresce upon hybridization, Nat Biotechnol 1996; 14: 303-308.
Holland, et al., Detection of specific polymerase chain reaction product by utilizing the 5'-3' exonuclease activity of Thermus aquaticus DNA polymerase. PNAS 1991; 88: 7276-7280.
Trinh, et al., DNA methylation analysis by MethyLight technology. Methods 2001; 25: 456-462.
Watson, et al., Single nucleotide primer extension (SNuPE) analysis of the G6PD gene in somatic cells and oocytes of a kangaroo (*Macropus robustus*), Genet Res 2000; 75: 269-274.
De Capoa, et al., Computer-assisted analysis of methylation status of individual interphase nuclei in human cultured cells. Cytometry 1998; 31: 85-92.
Tsao, et al., Emerging personalized approaches for the management of advanced urothelial carinoma. Expert Rev Anticancer Ther 2012; 12: 1527-1543.
Ma, et al., Engulfment Protein GULP is Regulator of Transforming Growth Factor-β Response in Ovarian Cells. Journal of Biochemistry 2012; 287: 20636-20651.
Xylinas, et al., Urine Markers for detection and surveillance of bladder cancer. Urol Oncol 2014; 32: 222-229.
Xylinas, et al., Blood- and tissue-based biomarkers for prediction of outcomes in urothelial carcinoma of the bladder. Urol Oncol 2014; 32: 230-242.
Goodison, et al., Bladder Cancer Detection and Monitoring: Assessment of Urine- and Blood-Based Marker Tests. Mol Diagn Ther 2013;17:71-84.

* cited by examiner

*Primary Examiner* — Juliet C Switzer
(74) *Attorney, Agent, or Firm* — Johns Hopkins Technology Ventures

(57) ABSTRACT

The invention provides methods for detecting a cellular proliferative disorder (e.g., urothelial cancer) in a subject by assessing the methylation status of the GULP1 promoter in a nucleic acid sample. The methods of the invention are useful for diagnostic, prognostic as well as therapeutic regimen predictions.

22 Claims, 8 Drawing Sheets

Specification includes a Sequence Listing.

UROTHELIAL CANCER AND METHODS OF DETECTION AND TARGETED THERAPY

RELATED APPLICATION DATA

This application claims the benefit of priority under 35 U.S.C. § 119(e) of U.S. Provisional Patent Application Ser. No. 62/134,447, filed Mar. 17, 2015, the entire contents of which is incorporated herein by reference in its entirety.

STATEMENT OF GOVERNMENT SUPPORT

This invention was made with government support under grant number CA163594 awarded by the National Institutes of Health. The government has certain rights in this invention.

BACKGROUND OF THE INVENTION

Field of the Invention

The invention relates generally to methods for diagnosing and treating cancer and more specifically to methods for detecting, diagnosing and treating urothelial cancers.

Background Information

Urothelial carcinoma (UC) is the most common cancer of the urinary tract, ranking fifth cancer in men and ninth women in Western countries, with 150,000 deaths per year worldwide. There are two main subgroups of UC: the more common non-muscle-invasive urothelial carcinoma (NMIUC)(about 75% of newly diagnosed cases), which is usually associated with a favorable prognosis but high risk of recurrence, and muscle-invasive urothelial carcinoma (MIUC) which is less prevalent but typically associated with a relatively poor prognosis. Considering the high recurrence rate of UC and the need for the expensive and resource-intensive cystoscopy procedure, UC carries the greatest lifetime treatment cost for each patient diagnosed. So, the ability to efficiently detect and follow-up UC is crucial because treatment options and their efficacy vary profoundly depending on the clinical stage in which diagnosis is accomplished. Indeed, NMIUC standard therapy consists of transurethral resection (TUR), followed by instillation of chemotherapeutic agent or intravesical delivery of bacillus Calmette-Guerin (BCG) in the case of high-recurrence expected. On the other hand, MIUC patients are normally treated with cystectomy, with or without neoadjuvant chemotherapy. However, overall survival largely vary depending on the tumor stage, and treatment options have not improved substantially in recent years. So there is still room to understand the biology of UC in order to characterize the relevant UC specific deregulated pathways, to develop new biomarker for the surveillance of UC and ultimately improve its treatment options.

PTB Domain-Containing Engulfment Adaptor Protein1 (GULP1) is the human homologue of CED (*Caenorhabditis elegans* death)-6, whose function in engulfment is highly conserved among species. GULP1 acts as a promoter of phagocytosis in human macrophages and might function as a signaling adaptor downstream of CED-1. It has been shown that in *C. elegans*, CED1, CED6, and CED7 are required for actin reorganization around the apoptotic cell corpse, and that CED1 and CED6 colocalize with each other and with actin around the dead cell. Furthermore it was found that the CED10 GTPase acts genetically downstream of these proteins to mediate corpse removal, functionally linking the 2 engulfment pathways and identifying the CED1, CED6, and CED7 signaling module as upstream regulators of Rae activation.

Cigarette smoking (CS) is the well-established UC risk factor, and contributes up to 50% of UC occurrence in men and 20% in women. CS produces reactive oxygen species (ROS), which can be accumulated in the bladder. Previous studies supported that that NOX2-ROS signaling could be one of the major pathway of urothelial carcinogenesis. The most important pathway with ROS scavenger activity is the one orchestrated by the Nrf2/Keap1 axis. Nuclear factor E2-related factor 2 (Nrf2) is a transcription factor that upregulates the expression of ~200 genes to combat oxidative and electrophilic stress, upon release from its ubiquitin ligase Keap1 and translocation to the nucleus. Contrasting with the protective role in response to CS, arsenic exposure and other environmentally-related carcinogenic compounds in different tissue types, Nrf2 function may be potentially fatal if constitutively activated because it could confer growth advantage under stress conditions (REF). Under normal physiological conditions, Nrf2 is bound to Kelch-like ECH-associated protein-1 (Keap1) and thereby sequestered in the cytoplasm in association with the actin cytoskeleton, a physiologic function that also perform by GULP1. Although Nrf2 and Keap1 genetic and epigenetic alterations have been found in many solid cancers as a permanent activation of an adaptive response and activation of many Nrf2 targets and impaired Keap1 activity and somatic mutation of Nrf2 lead to full Nrf2 activation, which induce cancer cell proliferation and chemoresistance, no epigenetic and biological study has been performed for GULP1 in contrast to NRF2/Keap1 signaling axis.

It has been shown that genetic and epigenetic changes contribute to the development and progression of tumor cells. Epigenetic alterations in promoter methylation and histone acetylation have been associated with cancer-specific expression differences in human malignancies. Methylation has been primarily considered as a mechanism of tumor suppressor gene (TSG) inactivation, and comprehensive whole-genome profiling approaches to promoter hypermethylation have identified multiple novel putative TSGs silenced by promoter hypermethylation.

Understanding the epigenetic changes that lead to cancer progression will help unravel key biologic processes that lead to cancer formation. Thus, there is a need to find molecular markers that will: a) help determine the risk of developing cancer to consider appropriate preventive interventions; b) help detect cancers early when they are amenable to surgical cure; c) help to predict response of a particular therapy (such as paclitaxel); and d) help to determine the overall outcome of a cancer patient.

SUMMARY OF THE INVENTION

The present invention is based on the discovery that some genes have regulatory regions, or promoters, that are hypermethylated in cancer. As a result, typically the gene expression is down-regulated and in the case of a tumor suppressor gene, this can be a direct cause for cancer cell growth. This discovery is useful for cancer screening, risk-assessment, prognosis, and identification of subjects responsive to a therapeutic regimen. Accordingly, in part there are provided methods for detecting a cellular proliferative disorder (e.g., urothelial cancer) in a subject. The methods of the invention are useful for diagnostic, prognostic as well therapeutic regimen predictions and interventions.

In one aspect, the invention provides a method for diagnosing urothelial cancer in a subject having or at risk of developing urothelial cancer. The method includes determining the methylation state of a gene or a regulatory region of the GULP1 gene in a sample from a subject having or suspected of having a urothelial cancer. Such cancers include but are not limited to carcinoma of the bladder, ureters, kidney, or renal pelvis and associated tissues and organs.

A hypermethylated state, as compared to a corresponding normal cell, is indicative of a subject having or at risk of developing urothelial cancer. In one embodiment, the method includes contacting a nucleic acid-containing sample from cells of the subject with an agent that provides a determination of the methylation state of a regulatory region of a GULP1 gene, wherein the regulatory region is hypermethylated in a cell undergoing unregulated cell growth as compared to a corresponding normal cell; and identifying hypermethylation of the regulatory region in the nucleic acid-containing sample, as compared to the same region of the regulatory region in a subject not having urothelial cancer, wherein hypermethylation is indicative of a subject having or at risk of developing urothelial cancer.

In another aspect, the invention provides a method for diagnosing cancer in a subject having or at risk of developing a cell proliferative disorder. The method includes determining the methylation state of the regulatory region of the GULP1 gene. A hypermethylated state, as compared to a corresponding normal cell, is indicative of a subject having or at risk of developing a cell proliferative disorder. In one aspect the method includes contacting a nucleic acid-containing sample from cells of the subject with an agent that provides a determination of the methylation state of the GULP1 regulatory region (e.g., promoter) of a gene, wherein the regulatory region is hypermethylated in a cell undergoing unregulated cell growth as compared to a corresponding normal cell; and identifying hypermethylation of the regulatory region in the nucleic acid-containing sample, as compared to the same region of the regulatory region in a subject not having urothelial cancer, wherein hypermethylation is indicative of a subject having or at risk of developing a cell proliferative disorder.

In another aspect, the invention provides a method of determining the prognosis of a subject having urothelial cancer. The method includes determining the methylation state of a gene or a regulatory region of the GULP1 gene. A hypermethylated state, as compared to a corresponding normal cell in the subject or a subject not having the disorder, is indicative of a poor prognosis.

In another aspect, the invention provides a method of determining the prognosis of a subject having cancer. The method includes determining the methylation state of the regulatory region of GULP1 in a nucleic acid sample from the subject. A hypermethylated state, as compared to a corresponding normal cell in the subject or a subject not having the disorder, is indicative of a poor prognosis.

In another aspect, the invention provides a method of treating cancer or ameliorating symptoms associated with urothelial cancer in a subject in need thereof. The method includes administering to the subject an agent that demethylates a regulatory region of the GULP1 gene. Demethylation of the regulatory region of GULP1 that is in a hypermethylated state, as compared to that of a subject not having urothelial cancer, increases expression of the GULP1 gene or regulatory region, thereby ameliorating the symptoms associated with urothelial cancer.

In another aspect, the invention provides a method for determining whether a subject is responsive to a particular therapeutic regimen. The method includes determining the methylation state of a gene or a regulatory region of GULP1. A hypermethylated state of the GULP1 promoter/regulatory region, as compared with that of a normal subject, is indicative of a subject who may be responsive to the therapeutic regimen. In one embodiment, the therapeutic regimen is administration of one or more chemotherapeutic agents alone or in combination with one or more demethylating agents such as, but not limited to, 5-azacytidine, 5-aza-2-deoxycytidine and zebularine. In another embodiment, the therapeutic regimen is administration of cisplatin and/or paclitaxel.

In another aspect, the invention provides a method of treating a urothelial cell proliferative disorder associated with GULP1 in a subject. The method includes administering to a subject having or at risk of having the urothelial cell proliferative disorder with an agent that inhibits activation of Nrf2 pathway, thereby treating the urothelial cell proliferative disorder associated with GULP1 in the subject. In embodiments, the agent is administered with a chemotherapeutic agent, such as paclitaxel or cisplatin.

In another aspect, the invention provides a kit useful for the detection of a methylated CpG-containing nucleic acid in determining the methylation status of GULP1. In one embodiment, the kit includes a carrier element containing one or more containers comprising a first container containing a reagent that modifies unmethylated cytosine and a second container containing primers for amplification of the regulatory region or region of promoter of GULP1, wherein the primers distinguish between modified methylated and unmethylated nucleic acid.

DETAILED DESCRIPTION OF THE INVENTION

Figures 1A, 1B, 1C, 1D, 1E, 1F:
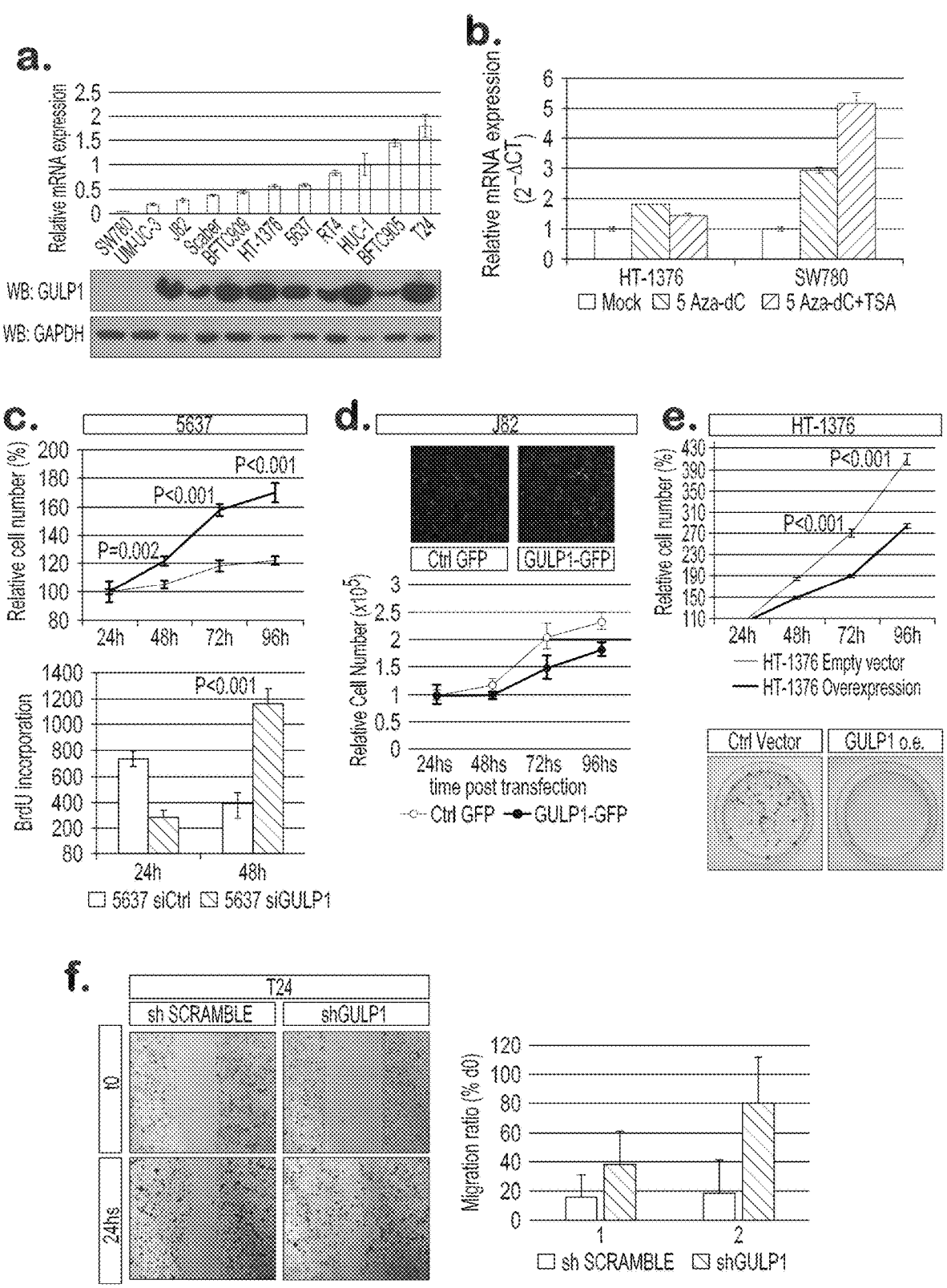
FIGS. 1*a*-1*f* are pictorial and graphical representations depicting experimental results generally relating to GULP1 down-regulation.

The present invention is based on the discovery that the GULP1 gene promoter or regulatory region is hypermethylated in urothelial cancers. GULP1 is a tumor suppressor gene, thus transcriptional down-regulation appears to be associated with cancer.

Before the present compositions and methods are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

It has been shown that genetic changes, which include deletions, amplifications, and mutations in DNA sequence, and epigenetic changes, which refer to heritable changes in the gene expression that occur without changes to the DNA sequence, contribute to the development and progression of tumor cells.

In relation to the present invention, GULP1 is identified as a novel tumor suppressor gene (TSG) selectively silenced during urothelial cancer (UC) progression through promoter hypermethylation (PH) analyzed by quantitative methylation specific PCR and novel methylation specific digital droplet PCR (ddPCR) assay. Numerous cell based assays revealed that GULP1 silencing confers growth advantage to tumor cells. Further mechanistic analysis revealed that GULP1 has a crucial role in the regulation of Nrf2-KEAP1 axis, maintaining actin cytoskeleton architecture and helping Keap1 to scaffold Nrf2 in the cytoplasm. Moreover, GULP1 silencing induces constitutive activation of Nrf2 target signature, responsible for chemoresistance of UCs. Additionally, GULP1 PH was analyzed and expression in cisplatin-based therapy responsive and resistant primary UC samples, and in isogenic cisplatin sensitive and resistant T24 cell lines. Interestingly, GULP1 expression was lower in both resistant primary UC samples and resistant T24 cell line. Altogether, the findings determined that GULP1 is an epigenetically silenced potential TSG in UC and GULP1 expression and/or PH may guide in selecting candidate patients for cisplatin based neo-adjuvant therapy.

Urothelial carcinoma (UC) is one of the most costly cancers to treat and requires new effective and less-invasive detection tests to improve its therapy because it largely varies for each clinical stage. Limited improvements in the disease-free survival rates have been accomplished in the past 20 years for both non-muscle invasive UC (NMIUC) and muscle-invasive UC (MIUC). The invention proposes the analysis of GULP1 promoter hypermathylation/expression levels as a diagnostic marker to foresee constitutive Nrf2 activation responsible for chemoresistance and therefore to decide whether cisplatin based neoadjuvant therapy could be considered as a therapeutic option with or without contemporary Nrf2 inhibition.

In one aspect of the invention, there are provided methods for identifying a cell that exhibits or is predisposed to exhibiting unregulated growth. The method includes determining the methylation state of a regulatory region of GULP1 in nucleic acid obtained from a sample from a subject having or suspected of having cancer, wherein the promoter is hypermethylated as compared to a corresponding normal cell not exhibiting unregulated growth, thereby identifying the cell as exhibiting or predisposed to exhibiting unregulated growth.

As used herein, the term "hypermethylated" refers to the addition of one or more methyl groups to a cytosine ring in a DNA sequence to form methyl cytosine as compared to a "normal" gene. Such methylations typically only occur on cytosines that precede a guanosine in the DNA sequence, which is commonly known as a CpG dinucleotide. There are CpG-rich regions known as CpG islands which span the 5' end region (e.g., promoter, untranslated region and exon 1) of many genes and are usually unmethylated in normal cells. The methylation patterns of cancer cells are altered as compared to the corresponding normal cells, undergoing global DNA hypomethylation as well as hypermethylation of CpG islands. Hypomethylation has been hypothesized to contribute to oncogenesis by transcriptional activation of oncogenes and latent transposons, or by chromosome instability. Aberrant promoter hypermethylation and histone modification, leading to transcriptional inactivation and gene silencing, is a common phenomenon in human cancer cells and likely one of the earliest events in carcinogenesis. As such, hypermethylation of CpG islands in gene promoter regions is a frequent mechanism of inactivation of tumor suppressor genes.

As used herein "corresponding normal cells" means cells that are from the same organ and of the same type as the cells being examined, but are known to be free from the disorder being diagnosed or treated. In one aspect, the corresponding normal cells comprise a sample of cells obtained from a healthy individual. Such corresponding normal cells can, but need not be, from an individual that is age-matched to the individual providing the cells being examined. In another aspect, the corresponding normal cells comprise a sample of cells obtained from an otherwise healthy portion of tissue (e.g., bladder, kidney, ureter) of a subject having urothelial cancer.

In one aspect, the invention provides a method for detecting a urothelial cell proliferative disorder associated with engulfment adaptor PTB domain containing 1 (GULP1) in a subject. The method includes: a) contacting a target nucleic acid in a sample of urothelial tissue or biological fluid from the subject containing urothelial cells with a reagent which detects GULP1, wherein the reagent detects methylation of the promoter region of GULP1 when the target nucleic acid is DNA; and b) detecting GULP1 target nucleic acid, wherein hypermethylation of the promoter of GULP1 DNA as compared to a corresponding normal cell, is indicative of a urothelial cell proliferative disorder.

In another aspect, the invention provides a method for detecting a urothelial cell proliferative disorder associated with engulfment adaptor FIB domain containing 1 (GULP1) in a subject. The method includes a) contacting a target nucleic acid in a sample of urothelial tissue or biological fluid from the subject containing urothelial cells with a reagent which detects GULP1, wherein the reagent detects the level of GULP1 RNA when the target nucleic acid is RNA; and b) detecting GULP1 target nucleic acid, wherein decreased levels of GULP1 RNA, as compared with the level of GULP1 RNA in a corresponding normal cell, is indicative of a urothelial cell proliferative disorder.

The term "GULP1 gene", "GULP1 rna, or "GULP1 protein", as used herein, refers to any naturally occurring variants or mutants, interspecies homologs or orthologs, or man-made variants of human GULP1 gene, GULP1 rna or GULP1 protein. The human GULP1 gene is located on chromosome 2 at 2q32.3-q33. The genomic sequence of a human wild-type GULP1 gene is set forth in NCBI Reference Sequence NC_000002.12 having associated Gene ID: 51454, which are incorporated herein by reference. A GULP1 gene includes a nucleotide sequence having at least 80%, 90%, 95%, 96%, 97%, 98%, 99% or higher sequence identity to the GULP1 gene of NCBI Reference Sequence NC_000002.12. A GULP1 protein within the meaning of this application is encoded by the GULP1 gene including the 304-amino acid GULP1 protein set forth in GenBank Accession No. NM_016315, incorporated herein by reference, or a protein having at least 80%, 90%, 95%, 96%, 97%, 98%, 99% or higher sequence identity to such GULP1 protein. A GULP1 rna within the meaning of this application encodes a GULP1 protein, and includes GULP1 rnas set forth in GenBank Accession Nos. XM_011511335.1, XM_011511334.1, XM_006712590.2, XM_006712589.2, XM_011511333.1, XM_011511332.1, XM_011511331.1, XM_011511330.1, XM_011511329.1, XM_011511328.1, XM_006712584.2, XM_011511327.1, XM_006712583.2, XM_006712580.2, XM_006712585.1, XM_006712582.1, XM_006712581.1, NR_045562.1, NR_045563.1, NM_016315.3, NM_001252669.1, NM_001252668.1, incorporated herein by reference, or a nucleotide sequence having at least 80%, 90%, 95%, 96%, 97%, 98%, 99% or higher sequence identity to such GULP1 rnas.

Accordingly, the present invention is designed to profile methylation alterations on promoter regions of selected genes, e.g., GULP1, in urothelial tumors with the aim of identifying candidate markers for diagnosis and prognosis of the disease, with sensitivity and specificity necessary to identify subjects with early asymptomatic urothelial cancer, as well as disease monitoring, therapeutic prediction and new targets for therapy.

As used herein, the term "cell proliferative disorder" refers to malignant as well as non-malignant cell populations which often differ from the surrounding tissue both morphologically and genotypically. In some embodiments, the cell proliferative disorder is a cancer. In particular embodiments the cancer may be a carcinoma. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, urothelial cancer, testicular cancer, bladder cancer, cervical cancer, and adenomas. In an illustrative example in this invention, the cancer is urothelial cancer, i.e., urothelial carcinoma.

The term "bisulfate" as used herein encompasses all types of bisulfites, such as sodium bisulfate, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C.fwdarw.U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. For any one "CpG-containing genomic sequence" at a given location, e.g., within a region of the human GULP1 genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non-protein-coding sequence (such as a transcription promoter), or a combination thereof.

The nucleic acid-containing sample for use in the invention methods may be virtually any biological sample that contains nucleic acids from the subject. The biological sample can be a tissue sample which contains 1 to 10,000,000, 1000 to 10,000,000, or 1,000,000 to 10,000,000 somatic cells. However, it is possible to obtain samples that contain smaller numbers of cells, even a single cell in embodiments that utilize an amplification protocol such as PCR. The sample need not contain any intact cells, so long as it contains sufficient material (e.g., protein or genetic material, such as RNA or DNA) to assess methylation status or gene expression levels.

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. In one embodiment, the biological or tissue sample can be drawn from any tissue that is susceptible to cancer. Thus, exemplary samples include, but are not limited to, a tissue sample, a frozen tissue sample, a biopsy specimen, a surgical specimen, a cytological specimen, whole blood, bone marrow, serum, plasma, urine, or ejaculate.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

Numerous methods for analyzing methylation status of a gene or regulatory region are known in the art and can be used in the methods of the present invention to identify hypermethylation. As illustrated in the Examples herein, analysis of methylation can be performed by bisulfite genomic sequencing.

Bisulfite ions, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

In another embodiment, the gene is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding non-methylated gene sequence, gaps are apparent at positions in the test gene contained methylated cytosine residues. As such, the presence of gaps is indicative of methylation of a cytosine residue in the CpG dinucleotide in the target gene of the test cell.

Modified products can be detected directly, or after a further reaction that creates products that are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means which are reliant on specific sequences can be used, including but not limited to hybridization, amplification, sequencing, and ligase chain reaction. Combinations of such techniques can be used as is desired.

In another example, methylation status may be assessed using real-time methylation specific PCR (QMSP). For example, the methylation level of the promoter region of one or more of the target genes can be determined by determining the amplification level of the promoter region of the target gene based on amplification-mediated displacement of one or more probes whose binding sites are located within the amplicon. In general, real-time quantitative methylation specific PCR is based on the continuous monitoring of a progressive fluorogenic PCR by an optical system. Such PCR systems are well-known in the art and usually use two amplification primers and an additional amplicon-specific, fluorogenic hybridization probe that specifically binds to a site within the amplicon. The probe can include one or more fluorescence labeled moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated.

In other embodiments, hypermethylation can be identified through nucleic acid sequencing after bisulfite treatment to determine whether a uracil or a cytosine is present at a specific location within a gene or regulatory region. If uracil is present after bisulfite treatment, then the nucleotide was unmethylated. Hypermethylation is present when there is a measurable increase in methylation.

In another embodiment, the method for analyzing methylation of the target gene can include amplification using a primer pair specific for methylated residues within the target gene. Thus, selective hybridization or binding of at least one of the primers is dependent on the methylation state of the target DNA sequence (Herman et al., *Proc. Natl. Acad. Sci. USA*, 93:9821 (1996)). For example, the amplification reaction can be preceded by bisulfite treatment, and the primers can selectively hybridize to target sequences in a manner that is dependent on bisulfite treatment. As such, one primer can selectively bind to a target sequence only when one or more bases of the target sequence is altered by bisulfite treatment, thereby being specific for a methylated target sequence.

Other methods are known in the art for determining methylation status of a target gene, including, but not limited to, array-based methylation analysis (see Gitan et al., *Genome Res* 12:158-64, 2002) and Southern blot analysis.

Methods using an amplification reaction can utilize a real-time detection amplification procedure. For example, the method can utilize molecular beacon technology (Tyagi S., et al., *Nature Biotechnology*, 14: 303 (1996)) or TAQMAN™ technology (Holland, P. M., et al., *Proc. Natl. Acad. Sci. USA,* 88:7276 (1991)).

In addition, methyl light (Trinh, et al. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson, et al., *Genet Res.* 75(3):269-74 (2000)) can be used in the methods of the present invention related to identifying altered methylation of the genes or regulatory regions provided herein. Additionally, methyl light, methyl heavy, and array-based methylation analysis can be performed, by using bisulfate treated DNA that is then PCR-amplified, against microarrays of oligonucleotide target sequences with the various forms corresponding to unmethylated and methylated DNA.

The degree of methylation in the DNA associated with the gene or genes or regulatory regions thereof, may be measured by fluorescent in situ hybridization (FISH) by means of probes that identify and differentiate between genomic DNAs, which exhibit different degrees of DNA methylation. FISH is described in Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Gianotti P., Marotta, M. R., Spano A., Rocchi M., Archidiacono N., Niveleau A. Computer-assisted analysis of methylation status of individual interphase nuclei in human cultured cells. *Cytometry.* 31:85-92, 1998, which is incorporated herein by reference.

In another embodiment, methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Alternatively, chemical reagents can be used that selectively modify either the methylated or non-methylated form of CpG dinucleotide motifs.

In some embodiments, hypermethylation of the target gene is detected by detecting decreased expression of the that gene. Expression of a gene can be assessed using any means known in the art. Typically expression is assessed and compared in test samples and control samples which may be normal, non-malignant cells. The test samples may contain cancer cells or pre-cancer cells or nucleic acids from the cells. Methods employing hybridization to nucleic acid probes can be employed for measuring specific mRNAs. Such methods include using nucleic acid probe arrays (microarray technology), in situ hybridization, and using Northern blots. Messenger RNA can also be assessed using amplification techniques, such as RT-PCR. Advances in genomic technologies now permit the simultaneous analysis of thousands of genes, although many are based on the same concept of specific probe-target hybridization. Sequencing-based methods are an alternative; these methods started with the use of expressed sequence tags (ESTs), and now include methods based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest. Moreover, specific proteins can be assessed using any convenient method including, but not limited to, immunoassays and immuno-cytochemistry. Most such methods will employ antibodies that are specific for the particular protein or protein fragments. The sequences of the mRNA (cDNA) and proteins of the target genes of the present invention are known in the art and publicly available.

As used herein, the tem' "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC: AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, a particular gene of interest, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

Gene expression levels also can be determined by quantification of a microRNA or gene transcript (e.g., mRNA). Commonly used methods known in the art for the quantification of mRNA expression in a sample include, without limitation, northern blotting and in situ hybridization; RNAse protection assays; and PCR-based methods, such as reverse transcription polymerase chain reaction (RT-PCR) and real time quantitative PCR (also referred to as qRT-PCR). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), and gene expression analysis by massively parallel signature sequencing (MPSS).

Some method embodiments involving the determination of mRNA levels utilize RNA (e.g., total RNA) isolated from a target sample, such a breast cancer tissue sample. General methods for RNA (e.g., total RNA) isolation are well known in the art and are disclosed in standard textbooks of molecular biology.

Differential gene expression also can be determined using microarray techniques. In these methods, specific binding partners, such as probes (including cDNAs or oligonucleotides) specific for RNAs of interest or antibodies specific for proteins of interest are plated, or arrayed, on a microchip substrate. The microarray is contacted with a sample containing one or more targets (e.g., microRNA, mRNA or protein) for one or more of the specific binding partners on the microarray. The arrayed specific binding partners form specific detectable interactions (e.g., hybridized or specifically bind to) their cognate targets in the sample of interest.

In some examples, differential gene expression is determined using in situ hybridization techniques, such as fluorescence in situ hybridization (FISH) or chromogen in situ hybridization (CISH). In these methods, specific binding partners, such as probes labeled with a fluorophore or chromogen specific for a target cDNA, microRNA or mRNA (e.g., a biomarker cDNA or mRNA molecule or microRNA molecule) is contacted with a sample, such as a breast cancer sample mounted on a substrate (e.g., glass slide). The specific binding partners form specific detectable interactions (e.g., hybridized to) their cognate targets in the sample. For example, hybridization between the probes and the target nucleic acid can be detected, for example by detecting a label associated with the probe. In some examples, microscopy, such as fluorescence microscopy, is used.

In yet another aspect, the invention provides methods of determining the prognosis of a subject having urothelial cancer. The method includes determining the methylation state of a GULP1 regulatory region in a nucleic acid sample from the subject. A comparison of the hypermethylation of the regulatory region, as compared to that of a corresponding normal cell in the subject or a subject not having the disorder, is indicative of a prognosis, wherein increased hypermethylation is indicative of a poor prognosis will decreased hypermethylation is indicative of cancer-free survival or regression. In embodiments, the subject is undergoing a therapeutic regimen, such as chemotherapy with paclitaxel or cisplatin.

In another embodiment, the method includes contacting a target nucleic acid in a sample of urothelial tissue or biological fluid from the subject containing urothelial cells with a reagent which detects GULP1, wherein the reagent detects the level of GULP1 RNA when the target nucleic acid is RNA, and wherein the contacting of the sample occurs prior to, simultaneously with and/or following a course of treatment; detecting GULP1 target nucleic acid; and providing a prognosis to the subject based on the detecting, increased levels of GULP1 RNA, as compared with the level of GULP1 RNA as compared to a reference sample of the subject, is indicative of an increase likelihood of cancer-free survival or regression in the subject. In embodiments, the subject is undergoing a therapeutic regimen, such as chemotherapy with paclitaxel or cisplatin.

The invention also provides a method for assigning a subject to a high-risk group for urothelial cancer, wherein the subject exhibits hypermethylation of a GULP1 regulatory region.

In some embodiments, the presently disclosed methods can comprise statistically analyzing the amounts of GULP1 gene methylation or expression. The statistical analysis can comprise applying a predetermined algorithm. The results of the algorithm can be employed to assign a subject to a group having a higher or lower likelihood of urothelial cancer.

A variety of algorithms can be employed in the presently disclosed methods. The algorithms employed are not limited to those described herein, but rather include algorithms as would be apparent to those of ordinary skill in the art upon a review of the instant disclosure.

In another aspect, the invention provides methods of identifying a cell that exhibits or is predisposed to exhibiting unregulated growth.

In another aspect, the invention provides methods of ameliorating symptoms associated with urothelial cancer in a subject in need thereof, for example by administering a demethylating agent, optionally in combination with a chemotherapeutic, such as paclitaxel or cisplatin. The signs or symptoms to be monitored will be characteristic of urothelial cancer and will be well known to the skilled clinician, as will the methods for monitoring the signs and conditions.

In another aspect, the invention provides a method of treating a urothelial cell proliferative disorder associated with GULP1 in a subject. The method includes administering to a subject having or at risk of having the urothelial cell proliferative disorder with an agent that inhibits activation of Nrf2 pathway, thereby treating the urothelial cell proliferative disorder associated with GULP1 in the subject. In embodiments, the agent is administered with a chemotherapeutic agent, such as paclitaxel or cisplatin.

By illustrating the correlation of suppressed expression of GULP1 protein and urothelial cancer, the present invention further provides a means for treating patients suffering from urothelial cancer: by way of increasing GULP1 protein expression or biological activity. As used herein, treatment of urothelial cancer encompasses reducing, reversing, lessening, or eliminating one or more of the symptoms of urothelial cancer, as well as preventing or delaying the onset of one or more of the relevant symptoms.

Increasing GULP1 Expression or Activity
Nucleic Acids Encoding GULP1 Proteins
Enhancement of GULP1 gene expression can be achieved through the use of nucleic acids encoding a functional GULP1 protein. Such nucleic acids can be single-stranded nucleic acids (such as mRNA) or double-stranded nucleic acids (such as DNA) that can translate into an active form of GULP1 protein under favorable conditions.

In one embodiment, the GULP1-encoding nucleic acid is provided in the form of an expression cassette, typically recombinantly produced, having a promoter operably linked to the polynucleotide sequence encoding the GULP1 protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the GULP1 protein expression in the target tissue, e.g., ureter epithelium. Since the human GULP1 gene cDNA sequence is known as provided above, one can derive a suitable GULP1-encoding nucleic acid from the sequence, species homologs, and variants of these sequences.

GULP1 Proteins

By directly administering an effective amount of an active GULP1 protein to a patient suffering from urothelial cancer and exhibiting suppressed GULP1 protein expression or activity, the disease may also be effectively treated. For example, this can be achieved by administering a recombinantly produced GULP1 protein possessing its biological activity to the patient suffering from urothelial cancer. Formulations and methods for delivering a protein- or polypeptide-based therapeutic agent are well known in the art.

Activators of GULP1 Protein

Increased GULP1 protein activity can be achieved with an agent that is capable of activating the expression of GULP1 protein or enhancing the activity of GULP1 protein. For example, a demethylating agent (e.g., 5-Aza, as discussed below) may be able to activate GULP1 gene expression by removing the suppression of GULP1 gene expression caused by methylation of the promoter region of this gene. Other activating agents may include transcriptional activators specific for the GULP1 promoter and/or enhancer. Such activating agents can be screened for and identified using the GULP1 expression assays described in the examples herein.

Agonists of the GULP1 protein, such as an activating antibody, are another kind of activators of the GULP1 protein. Such activators act by enhancing the biological activity of the GULP1 protein, typically (but not necessarily) by direct binding with the GULP1 protein and/or its interacting proteins. Preliminary screening for such agonists may start with a binding assay for identifying molecules that physically interact with GULP1 protein.

As used herein, the terms "administration" or "administering" are defined to include the act of providing a compound or pharmaceutical composition of the invention to a subject in need of treatment. Exemplary forms of administration include, but are not limited to, topical administration, and injections such as, without limitation, intravitreal, intravenous, intramuscular, intra-arterial, intra-thecal, intra-capsular, intra-orbital, intra-cardiac, intra-dermal, intra-peritoneal, trans-tracheal, sub-cutaneous, sub-cuticular, intra-articulare, sub-capsular, sub-arachnoid, intra-spinal and intra-sternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the compound or composition to treat urothelial cancer and/or ameliorate the symptoms associated therewith in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

As used herein, the term "ameliorating" or "treating" means that the clinical signs and/or the symptoms associated with cellular proliferative disorder (e.g., urothelial cancer) are lessened as a result of the actions performed. The signs or symptoms to be monitored will be characteristic of the cellular proliferative disorder (e.g., urothelial cancer) and will be well known to the skilled clinician, as will the methods for monitoring the signs and conditions. Also included in the definition of "ameliorating" or "treating" is the lessening of symptoms associated with urothelial cancer in subjects not yet diagnosed as having the specific cancer. As such, the methods may be used as a means for prophylactic therapy for a subject at risk of having urothelial cancer.

As used herein, the term "demethylating agent" is used to refer to any compound that can inhibit methylation, resulting in the expression of the previously hypermethylated silenced genes. Cytidine analogs such as 5-azacytidine (azacitidine) and 5-aza-2-deoxycytidine (decitabine) are the most commonly used demethylating agents. These compounds work by binding to the enzymes that catalyze the methylation reaction, DNA methyltransferases. Thus, in one embodiment, the demethylating agent is 5-azacytidine, 5-aza-2-deoxycytidine, or zebularine. In another embodiment, the demethylating agent is delivered locally to a tumor site or systemically by targeted drug delivery.

Agents that demethylate the hypermethylated gene or regulatory region of the gene can be contacted with cells in vitro or in vivo for the purpose of restoring normal gene expression to the cell. Once disease is established and a treatment protocol is initiated, the methods of the invention may be repeated on a regular basis to evaluate whether the methylation state of a gene or regulatory region thereof, in the subject begins to approximate that which is observed in a normal subject. Alternatively, or in addition thereto, the methods of the invention may be repeated on a regular basis to evaluate whether the symptoms associated with urothelial cancer have been decreased or ameliorated. The results obtained from successive assays may be used to show the efficacy of treatment over a period ranging from several days to months to years. Accordingly, the invention is also directed to methods for determining whether a subject is responsive to a particular therapeutic regimen. A comparison of the hypermethylation of the GULP1 regulatory region, as compared to that of a corresponding normal cell in the subject or a subject not having the disorder is indicative of a subject who is responsive to the therapeutic regimen.

In one embodiment, the therapeutic regimen is administration of one or more chemotherapeutic agent. In another embodiment, the therapeutic regimen is administration of one or more chemotherapeutic agents in combination with one or more demethylating agents.

Exemplary chemotherapeutic agents include, but are not limited to, antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecoline, etoposide, taxane, anthracycline antibiotic, doxorubicin, daunorubicin, carminomycin, epirubicin, idarubicin, mithoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-α, etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis. Thus, in one embodiment, the therapeutic regimen is administration of paclitaxel.

The materials for use in the methods of the invention are ideally suited for the preparation of a kit. As such, in another aspect, the invention provides a kit for detection of a methylated CpG-containing nucleic acid in determining the methylation status of GULP1 promoter region. Such a kit may comprise a carrier device containing one or more containers such as vials, tubes, and the like, each of the containers comprising one of the separate elements to be used in the method. The kit may contain reagents, as described above for differentially modifying methylated and non-methylated cytosine residues. One of the containers may include a probe which is or can be detectably labeled. Such probe may be a nucleic acid sequence specific for a promoter region associated with GULP1. The kit may also include a container comprising a reporter, such as an enzymatic, fluorescent, or radionucleotide label to identify the detectably labeled oligonucleotide probe.

In certain embodiments, the kit utilizes nucleic acid amplification in detecting the target nucleic acid. In such embodiments, the kit will typically contain both a forward and a reverse primer for each target gene. Such oligonucleotide primers are based upon identification of the flanking regions contiguous with the target nucleotide sequence. Accordingly, the kit may contain primers useful to amplify and screen a promoter region of a GULP1 gene.

In some kit embodiments, the primary detection means (e.g., nucleic acid probe, nucleic acid primer, or antibody) can be directly labeled, e.g., with a fluorophore, chromophore, or enzyme capable of producing a detectable product (such as alkaline phosphates, horseradish peroxidase and others commonly known in the art). Other kit embodiments will include secondary detection means; such as secondary antibodies (e.g., goat anti-rabbit antibodies, rabbit anti-mouse antibodies, anti-hapten antibodies) or non-antibody hapten-binding molecules (e.g., avidin or streptavidin). In some such instances, the secondary detection means will be directly labeled with a detectable moiety. In other instances, the secondary (or higher order) antibody will be conjugated to a hapten (such as biotin, DNP, and/or FITC), which is detectable by a detectably labeled cognate hapten binding molecule (e.g., streptavidin (SA) horseradish peroxidase, SA alkaline phosphatase, and/or SA QDot™). Some kit embodiments may include colorimetric reagents (e.g., DAB, and/or AEC) in suitable containers to be used in concert with primary or secondary (or higher order) detection means (e.g., antibodies) that are labeled with enzymes for the development of such colorimetric reagents.

In some embodiments, a kit includes positive or negative control samples, such as a cell line or tissue known to express or not express a particular biomarker.

In some embodiments, a kit includes instructional materials disclosing, for example, means of use of a probe or antibody that specifically binds a disclosed gene or its expression product (e.g., microRNA, mRNA or protein), or means of use for a particular primer or probe. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

Certain kit embodiments can include a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples). Such disposal means can include, without limitation, containers that are capable of containing leakage from discarded materials, such as plastic, metal or other impermeable bags, boxes or containers.

The kits can further include software. Software may include a training video that may provide additional support including demonstration of biomarker assays, examples of results, or educational materials for performing biomarker assays according to the invention.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Gulp1 as a Biomarker for Urothelial Carcinoma

Engulfment gene GULP1 is a functional tumor suppressor through influencing TGF-β pathway and is silenced by promoter methylation in urothelial carcinoma GULP1 functions as a cytoplasmic adaptor protein in the engulfment of apoptotic corpses and cells. It was also reported to be an adapter protein of LRP1 which is known to be a key regulator of TGF-β signaling. TGF-β signaling pathway is known to contribute to urothelial carcinoma (UC) development by increasing invasiveness and metastasis, and inducing epithelial to mescenchymal (EMT) transition. By an integrated genetic approach. GULP1 was recently identified as a potential tumor suppressor gene and epigenetically silenced in ovarian cancer. This example provides evidence of promoter methylation of GULP1 in urothelial carcinoma (UC) and provides a functional characterization of GULP1 in urothelial carcinogenesis.

GULP1 protein expression was first determined by immunohistochemistry on a customized muscle-invasive UC (MIUC) tissue-microarray. The mechanism of gene silencing was probed using quantitative methylation-specific PCR (QMSP). The association between GULP1 expression and promoter methylation was analyzed by using a subset of primary UC and UC cell lines. Effects of forced overexpression and siRNA-mediated GULP1-knockdown were measured by cell proliferation and colony forming assays. Western blot analysis was performed for several key molecules to determine the effect of GULP1 modulation in the respective pathways.

Complete loss of GULP1 expression was observed in 89 out of 104 MIUC (85.6%). In primary tumor tissues and cell lines, promoter methylation of GULP1 was inversely correlated with GULP1 expression (see Table 1 below) and reactivation of GULP1 was observed by 5-aza-dC treatment of UC cell lines. Additionally QMSP assay of GULP1 was performed for 98 primary UC tissues of different cell types and 21 normal urothelial samples. Initial analysis by using an empiric cut off value revealed GULP1 promoter methylation was significantly associated with UC (P=0.007, Fisher's exact test). To deter mine the feasibility of GULP1 QMSP assay for non-invasive detection of UC using urine DNA, urine from 58 UC patients and 46 healthy people was tested. As expected, 33 out of 58 (56.9%) UC cases were methylation positive while a very low level of methylation was detected in 4 out of 46 urine control samples (8.7%) (P<0.001, Fisher's exact test). Effect of in vitro modulation of GULP1 was determined by MTT assay, BrdU assay and colony formation assay. The results consistently revealed that GULP1 had anti-proliferative activities.

In order to detect the pathways related to GULP1, RNA from T24 and shGULP1 transfected T24 cells were applied to the Cancer PathwayFinder™ Array (Qiagen). Heme oxygenase 1 (HMOX1) showed over 3 fold increase in expression in T24 shGULP1 cells. Other associated molecules altered due to GULP1 knock-down include TGF-β RI, p-Smad3C, p15 and LRP1.

In conclusion, GULP1 is a tumor suppressor in UC carcinogenesis and useful for non-invasive UC detection and targeting therapy.

Example 2

Gulp1 Down-Regulation in Urothelial Carcinoma

GULP1 gene was identified as a potential tumor suppressor gene (TSG) in ovarian cancer. In this example GULP1 expression and promoter methylations analysis was performed in multiple UC samples and biologically characterize GULP1 as a potential tumor suppressor gene. Although there are substantial findings that support GULP1 is involved in tumorigenesis, the role of GULP1 in UC was not known and most importantly the biological function and the pathways associated with GULP1 alterations was not well studied. The findings herein suggest that GULP1 is a UC specific methylated gene and GULP1 inactivation leads to activation of Nrf2 pathway in UC genesis.

Results

GULP1 Downregulation is Associated with Promoter Methylation in UC Cell Lines

GULP1 transcript expression was tested in a panel of 8 UC cell lines (5637, HT-1376, J82, SW780, UM-UC-3, T24, BFTC-905, BFTC-909), one squamous cell carcinoma cell line (Scaber), one transitional cell papilloma cell line (RT4) and one SV-40 immortalized normal urothelial cell line (HUC-1). Data showed low levels of GULP1 expression in a majority of poorly differentiated UC cell lines (UM-UC-3, J82, BFTC909, HT-1376, 5637) (FIG. 1a). Given the low/absent expression of GULP1 in many cultured UC cell lines and observation of GULP1 silencing due to promoter methylation in ovarian tumors, the contribution of promoter methylation to the downregulation of GULP1 expression was analyzed. To this end, HT-1376 and SW780 UC cells were treated with the global DNA demethylating drug 5-aza-deoxycytidine (5-azadC) with or without trichostatin A (TSA). Dense promoter methylation was observed in both the cell lines analyzed by bisulfite sequencing (FIG. 6a) and drugs treatment causes a several fold increase in GULP1 transcript which is also consistent with promoter demethylation (FIG. 1b and data not shown), These findings suggested that transcriptional silencing of GULP1 is mediated by promoter methylation in UC cells.

Frequency of GULP1 Promoter Methylation and Silencing are Significantly Higher in UC than in Non-Neoplastic Tissues.

Since epigenetic loss of GULP1 and, more generally, silencing of GULP1 may contribute to UC initiation and progression was hypothesized, the GULP1 expression and promoter methylation in multiple cohorts of clinical samples was analyzed. First, GULP1 expression analysis on 2 different UC Tissue-Micro-Arrays (TMA) was performed, one created from NMIUC and the other one created from MIUC samples. A total of 35 cases [35/90 (39%)] of NMIUCs showed silencing of GULP1 expression [9/34 (26.5%) of low grade papillary cases (pTa), 14/28 (50.0%) of high grade papillary cases (pTa) and 12/28 (42.9%) of lamina propria invasion cases (pT1)], while 91/106 (85.8%) of MIUCs showed no expression of GULP1. The GULP1 methylation frequency of MIUCs was significantly higher than that of each of NMIUC subtype ($P<0.001$ for all subtypes). Associations between several clinicopathological parameters (age at diagnosis, sex, tumor stage, recurrence and cancer-specific survival) and the expression of GULP1 in all NMIUCs and MIUCs samples was then examined. The analysis revealed that GULP1 silencing only correlated with tumor stage (NMIUC vs MIUC) ($P<0.001$, Fisher's exact test), but not with age, gender, and patient survival outcomes (data not shown).

After having observed a selective pressure of GULP1 silencing during tumor progression by immunohistochemical analysis, and observation of inverse association of GULP1 expression with promoter methylation in cell lines, the promoter methylation and expression of GULP1 analysis was extended in primary UC tissues to determine whether promoter methylation is associated with gene expression levels. To this end, immunohistochemical staining of 6 UC samples was first performed and it was observed that differential expression of GULP1 in different cellular component of UC and surrounding tissues. More particularly, muscle cells were almost always strongly positive, while normal epithelial cells were positive only towards the superficial luminal area of the epithelium. Cancer cells near the basement membrane did not show any expression of GULP1. To perform methylation study in these different cellular compartment, all the cellular component was carefully microdissected and separately, DNA extracted from normal epithelial cells, muscle cells and cancer cells from the representative 6 formalin fixed paraffin embedded (FFPE) slides. As expected, consistent with UC cell lines findings, it was observed that GULP1 promoter methylation was inversely correlated with GULP1 protein expression in these cellular component. Representative example of immunohistochemistry (IHC) was shown in FIG. 2b.

Figure 2A:
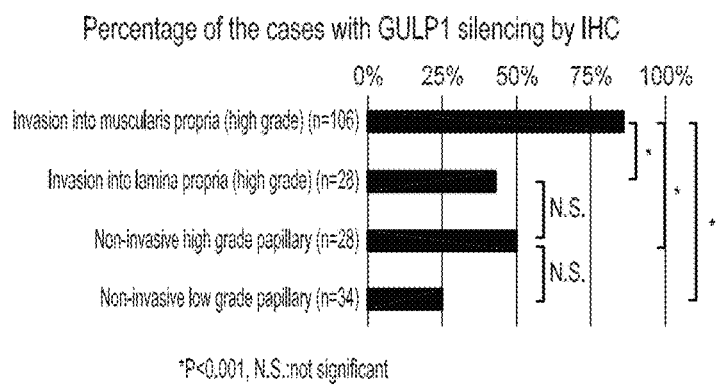
FIGS. 2*a*-2*c* are pictorial and graphical representations depicting experimental results generally relating to GULP1 down-regulation.
Figure 2B:
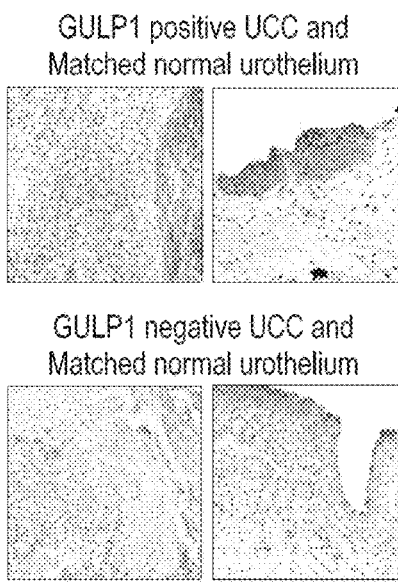
Figure 2C:
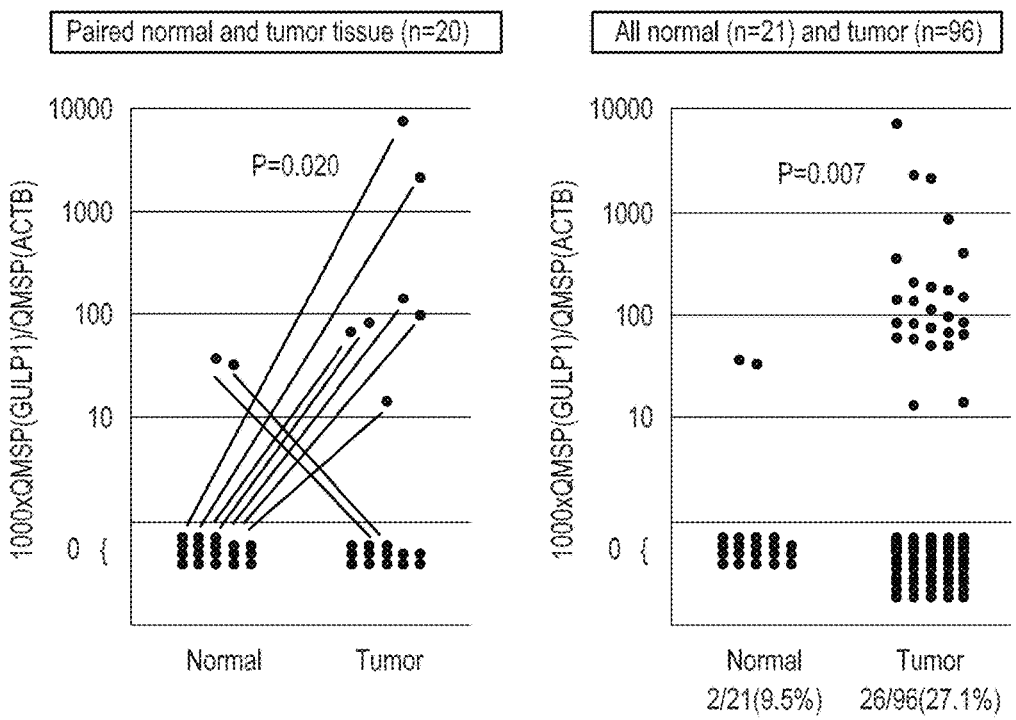

In order to confirm the importance of GULP1 promoter methylation during UC initiation and progression, and to evaluate if this phenomenon is clinically relevant, the methylation analysis was broadened to include a training and an independent test set of primary UC samples. QMSP assay was first employed on 20 primary tumors and matched normal samples and by using an empiric cut point, significantly higher frequency of GULP1 promoter methylation was observed in tumors 7/20 (35.0%) than in matched normal tissues 2/20 (10.0%) ($P=0.020$, Fisher's exact test, two-tailed) (FIG. 2c, left panel). FIG. 2c (right panel) showed quantitative methylation values are generally higher in tumor than paired normal. Subsequently, additional 76 primary tumors of different stages and grades were tested for GULP1 promoter methylation by QMSP, and by using the same cut-off value as initial cohort, the methylation frequency in this cohort of sample was 26/96 (27.1%) (FIG. 2c, right panel). Associations of GULP1 promoter methylation and clinicopathological factors were shown in Table 4. Tumor cases with GULP1 promoter methylation had a tendency of lymphatic/venous invasion ($P=0.066$) when compared with cases without GULP1 promoter methylation. To further explore the promoter methylation of GULP1 in early stage UC, a cohort of 54 low-grade papillary UC were tested and a percentage of samples were found to be methylated. In addition to analyzing primary UC tissues, the feasibility of GULP1 promoter methylation as a marker of non-invasive detection in a training and an independent test set was also determine. To this end we employed GULP1 QMSP assay on urine DNA samples from 58 UC patients and 46 healthy controls (training set). By an empiric cut-off value, GULP1 promoter methylation was detected in 33/58 (56.9%) of urine samples from UC cases, while it was detected only in 4/46 (8.7%) of control samples. Taken altogether, the GULP1 QMSP results identified GULP1 as a frequently UC specific methylated gene, and also has a potential to be included in the marker panel of non-invasive detection assay for UC.

Due to the wide differences between the frequency of GULP1 promoter methylation and the frequency of GULP1 silencing, as a pilot study, GULP1 promoter methylation was further analyzed by an ultrasensitive GULP1 promoter methylation specific ddPCR assay. This assay was employed on the same tumor tissue cohort (n=96) used previously for QMSP and as expected, methylation positive rate increased to 61.5% (59/96).

Validation of Expression and Methylation of GULP1 in the Cancer Genome Atlas Research Network Dataset.

To further validate the expression and promoter methylation of GULP1 in UC, the dataset from TCGA was utilized where genome-wide expression and methylation status is available. As the Illumina 450K Infinium™ platform used in TCGA analysis has probes for DNA methylation detection mostly at gene promoters, CpG sites of GULP1 promoter that were included in the QMSP and methylation-specific ddPCR assay were looked at. To match results from this and TCGA studies, CpG probes on the Infinium™ platform closest (<50 bp) to the sites analyzed in this study were searched for. Several CpG sites were found at GULP1 promoter whose sites analyzed by both methods nearly coincide. Methylation status of these CpG sites was used for a hierarchical clustering analysis. β-value of these CpG sites of GULP1 promoter were calculated. As of TCGA methylation data, we also acquired the data on total GULP1 mRNA expression levels from bladder cancer patients who had participated in the TCGA study. These expression data were retrieved from publicly available datasets after obtaining approval from the TCGA study group. All data files were stored in secure servers as per TCGA data handling requirements. A threshold for GULP1 expression was derived based on the observed mRNA expression levels in tumors as compared to matched normal bladder tissue GULP1 levels. The RNA-Seqv2 estimated raw counts for GULP1 from primary tumor and adjacent non-tumor samples were downloaded. Transcripts from the UCSC Known Genes Table, Refseq, Vega and Ensemble were used, and scores (number of tags in each transcript) were obtained from each sample. GULP1 expression level estimated raw counts were normalized using the Bioconductor R™ software package edgeR™. Scores were normalized with respect to total tags in the sample as well as total tags in the chromosome. Only the tags that overlap with transcripts were used in counting total tags. If the same tag is mapped to several places, a ratio is taken in counting. These estimation counts were obtained by TCGA using methods as published. Only those samples with available GULP1 expression data were retained for further analysis.

The distribution of GULP1 expression scores (ranging from 0 to 994.5) was assessed and it was noted that the distribution of GULP1 expression was non-normal, precluding the use of the expression scores directly as a continuous variable. After normalizing the GULP1 mRNA expression levels, a GULP1 normalized mRNA expression score was derived for each patient based on total normalized read counts. The GULP1 expression covariate was dichotomized as either high or low. To determine a threshold for GULP1 mRNA expression positivity, the distribution of GULP1 expression scores in normal versus tumor bladder tissues was compared to arrive at a cutoff threshold. As GULP1 mRNA is expressed in normal bladder tissues, a threshold such that most of all matching tumor and normal tissues had a tumor GULP1 mRNA level lower than the matching normal sample was used. This cut-off, which is equivalent to a normalized GULP1 expression score, was retained to dichotomize the GULP1 expression variable as GULP1-high or low tumors. The same procedure was performed for NFE2L2 and HMOX1.

From TCGA data set, a total of 85 from each of the high and low GULP1 expressed samples were identified, and the methylation data were available for all these samples (85 high and 85 low GULP1 expressed). The data showed that low GULP1 expressed samples are highly methylated as compared to high GULP1 expressed samples (P=0.0001).

Altogether the findings and TCGA data analysis identified GULP1 silenced by promoter methylation in UC, confirming previous published and unpublished results in other solid tumor types and pointing that its suppressive function in malignant cancer progression is an incisive mechanism for tumor development.

GULP1 Inhibits Proliferation, Clonogenicity and Motility Properties of UC Cell.

After having identified GULP1 as frequently methylated and down-regulated in bladder cancer cell lines and primary tumors, its biological function was elucidated using UC cell lines by forceful expression of GULP1 in HT-1376 (low-GULP1 expression) and SW780 cell lines (negative for GULP1 expression); and also by analyzing the effect of GULP1 knock-down in 5637 and T24 UC cell line which abundantly expressed GULP1. Relative mRNA expression levels of transfected cell lines (both for forceful expression and down-regulation) were confirmed by Q-RT-PCR (FIG. 6b).

Figures 6A, 6B, 6C, 6D:
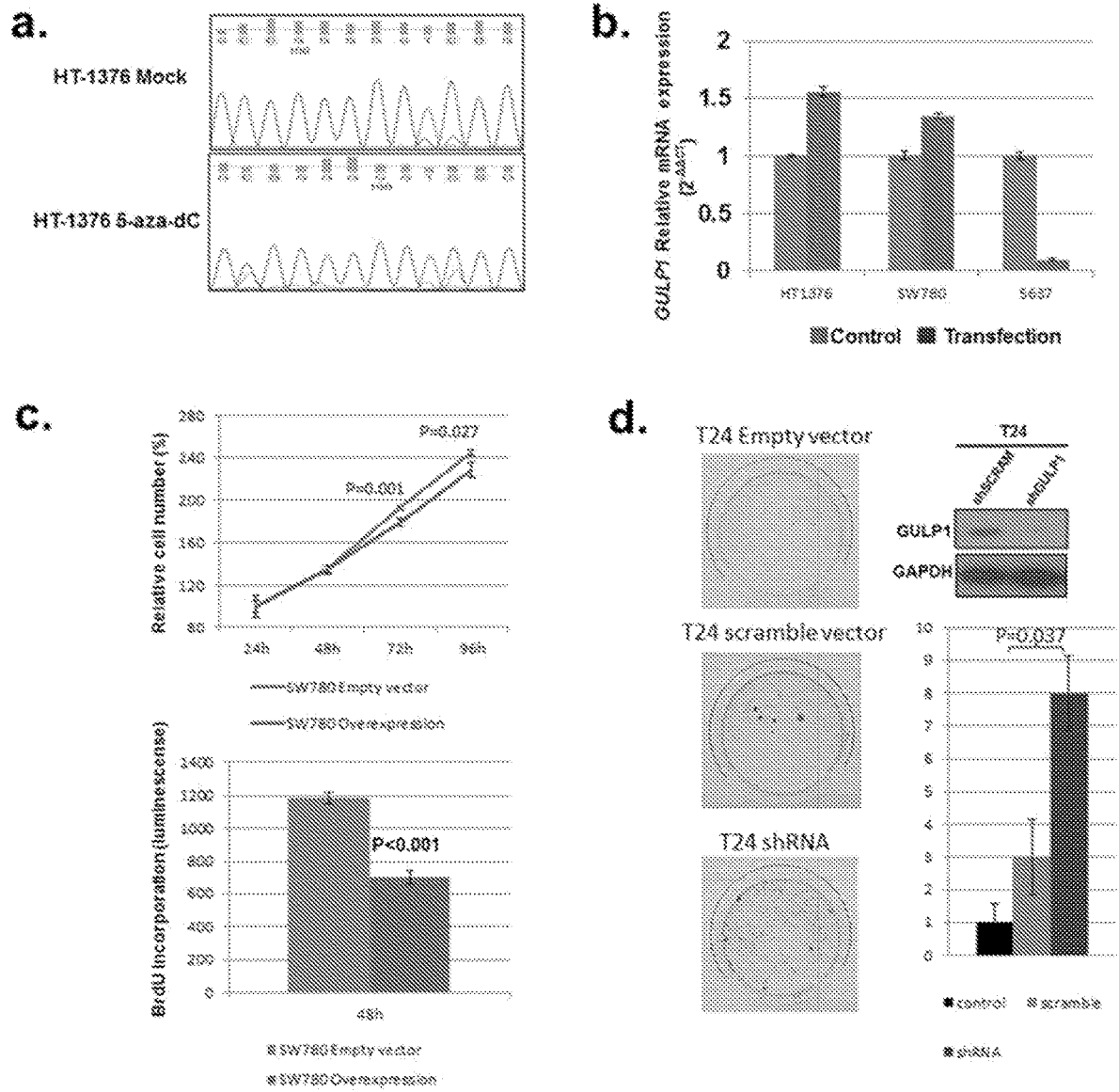
FIGS. 6*a*-6*d* are pictorial and graphical representations depicting experimental results generally relating to GULP1 down-regulation.

Cell proliferation was examined by [3-(4,5-dimethylthiazol-2-yl)-2,5-diphenyltetrazolium bromide)] (MTT) assay (FIGS. 1a and 1b) and BrdU incorporation assay (FIG. 6c). The data suggested that GULP1 overexpression implies significant decrease in both cell viability and cell proliferation and, on the contrary, GULP1 knock-down leads to significant increase of cell viability and cell proliferation. Moreover, in colony focus assays, GULP1 overexpression in HT-1376 cells showed potent long-term anti-proliferative effect by markedly reducing the colony-forming ability of the cells. To further confirm the anti-proliferative role of GULP1 in UC cells, we perform similar analysis in a GULP1-stable silenced T24 (T24 shGULP1) and T24 control (T24 scramble vector and empty vector) cells. As expected, in this cellular system the depletion of GULP1 protein increased the proliferation rate of the silenced cells (FIG. 6c) and conferred the clonogenicity advantage to GULP1 down-regulated cells (FIG. 6d).

Finally, to obtain further evidence regarding the potential tumor suppressive role of GULP1, the effect of its stable down-regulation on the migration and invasion abilities of T24 cells was tested. Interestingly, GULP1 silenced cells demonstrated more motile into the wound compared with control cells. However, no statistically significant increases in invasive activity following GULP1 knockdown (data not shown) was noticed. Similarly, we didn't observe any significant effect of GULP1 presence or silencing in the expression of epithelial (E-Cadherin) and mesenchymal (Vimentin) markers, described as a classical characteristic switch during tumor progression towards an invasive and metastatic phenotype (data not shown).

In summary, the above experiments reveal that modulation of GULP1 expression levels (overexpression and knockdown) in cultured UC cell lines have significant effect on important hallmarks of neoplastic transformation such as proliferation, cell migration and colony formation, each of these properties acquired by cancer cells during the tumor progression.

Inverse Correlation Between GULP1 and HMOX1 Expression in UC Cell Lines.

Figures 3A, 3B, 3C, 3D:
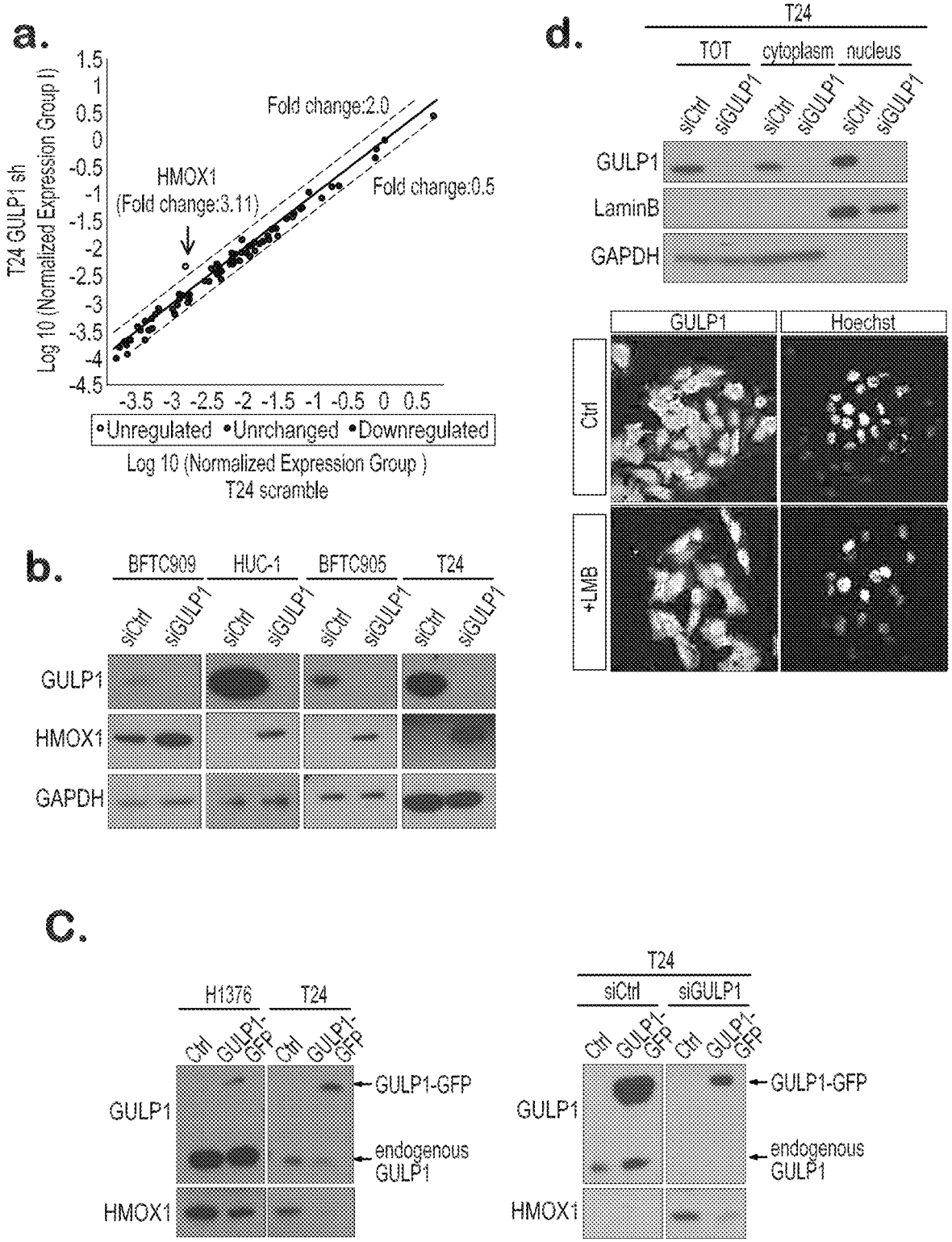
FIGS. 3*a*-3*d* are pictorial and graphical representations depicting experimental results generally relating to GULP1 down-regulation.

In order to gain mechanistic insights of GULP1 in urothelial carcinogenesis, we used $RT^2$ Profiler PCR Cancer PathwayFinder™ array (Qiagen) as described in the Materials and Methods section below. The pathway finder array contains 84 candidate genes that were known to be associated with angiogenesis, apoptosis, cell cycle, cellular senescence, EMT, hypoxia signaling, metabolism and telomerase activity. This approach allows us to perform the unbiased expression analysis of some key cancer associated genes in UC cells after GULP1 stable knockdown (T24 shGULP1 versus T24 shScramble stable clones). By this array analysis, heme oxygenase-1 (HMOX1) gene showed over 3 fold overexpression in GULP1 knock-down T24 cells compared to controls (FIG. 3a). By transient down-regulation of GULP1 expression by siRNA, this inverse correlation was further confirmed in 4 additional UC cell lines with high endogenous GULP1 expression (BFTC909, T24, BFTC905 and HUC-1 (FIG. 3b). Moreover, ectopic expression of GULP1 (GFP tagged to differentiate from the endogenous protein) led to a noticeable decrease of HMOX1 protein levels (FIG. 3c), further confirming the strong inverse correlation between GULP1 and HMOX1 proteins expression.

GULP1 Influence Nrf2 Signaling Pathway by Interacting with Keap1-Actin Cytoskeleton Protein Complex.

After having discovered inverse correlation of GULP1 and HMOX1 expression in several UC cell lines, the molecular mechanism responsible for this inverse correlation was further characterized. It was previously reported that HMOX1 expression is regulated positively by the transcriptional activator nuclear factor erythroid-derived 2 related factor 2 (NF2EL2, Nrf2) and negatively by the transcriptional repressor BTB and CNC homology 1 (Bach1), both competing to form heterodimers with the small-Maf protein and bind to Maf-recognition elements (MARE) in the HMOX1 promoter. Due to the importance of this cytoprotective mechanism, all the factors involved in the activation and repression of HMOX1 are tightly regulated, mainly at the post-translational level, through protein modifications and protein-protein interactions that mediate proteasomal degradation or nuclear-cytoplasmatic shuttling.

Since GULP1 protein was reported to be mainly localized in cytoplasm, it was desired to intensively characterize its pattern of subcellular localization in order to understand whether it could influence the localization and scaffold of Nrf2-Bach1 and eventually effect on HMOX1 activation via a dynamic subcellular localization. It was hypothesized that GULP1 effect on Nrf2 for its nuclear translocation and inactivation of GULP1 prohibit nuclear translocation of Nrf2.

Figures 8A, 8B, 8C, 8D, 8E:
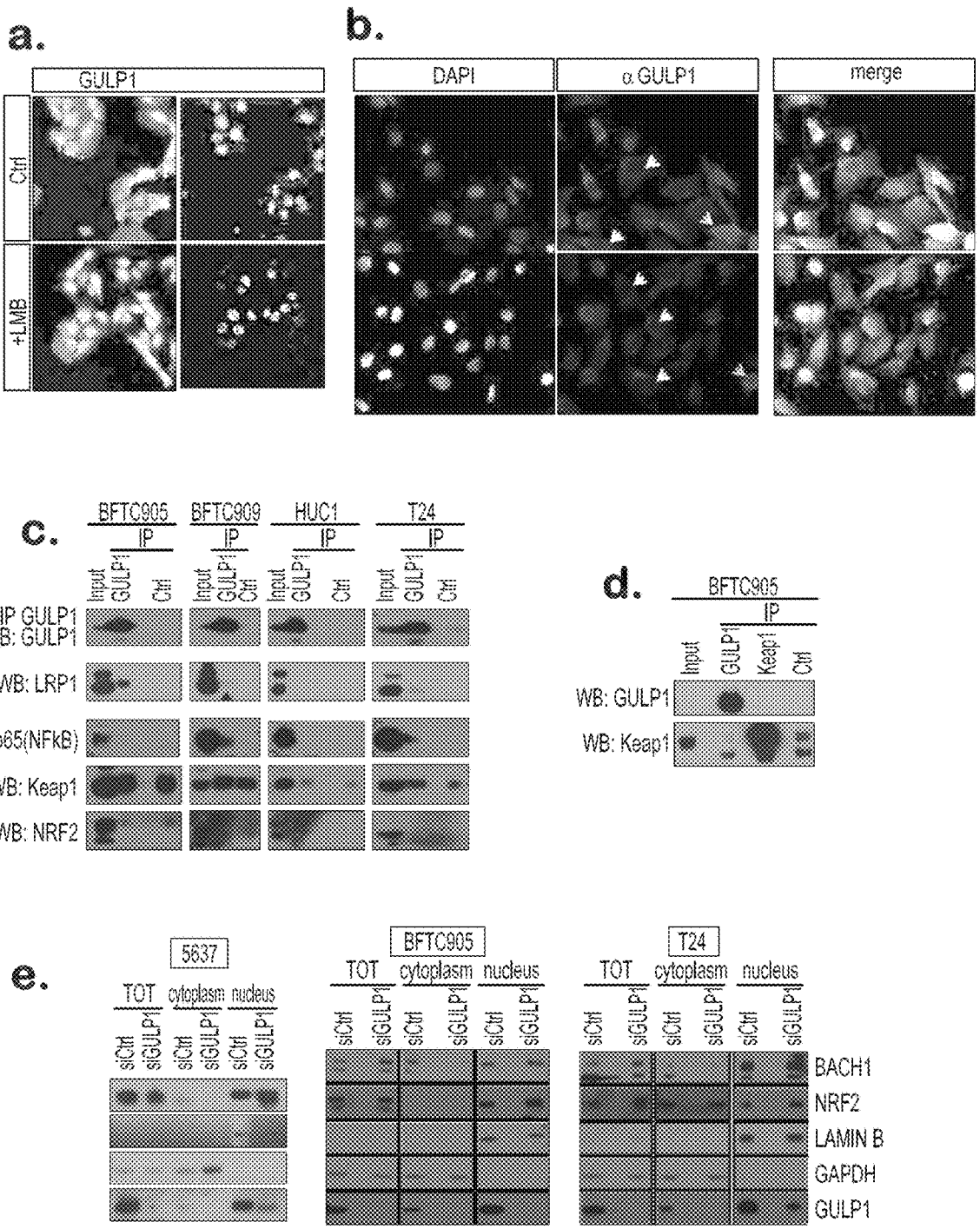
FIGS. 8*a*-8*e* are pictorial and graphical representations depicting experimental results generally relating to GULP1 down-regulation.

To this end, the subcellular localization of GULP1 was determined by confocal microscopy analysis and nuclear-cytoplasm fractionation experiments using T24 cell line. The findings indicate that GULP1 localized in both nucleus and cytoplasm (FIG. 3d, upper and lower panel, and FIG. 8a). Ubiquitous localization pattern of GULP1 was further confirmed by performing immunofluorescence and confocal microscopy analysis by using two different antibodies against GULP1 and upon blocking nuclear export machinery by Leptomycin B (LMB) treatment for 5 hours (T24 cells in FIG. 3d and FIG. 8b). The data indicate that blocking of nuclear export prevent GULP1 from going out from nucleus (FIG. 3d). Therefore, although further characterization is necessary, it is suggested that GULP1 could function as a shuttling molecule for Nrf2 between cytoplasm and nuclear compartment.

Figures 4A, 4B, 4C, 4D, 4E, 4F:
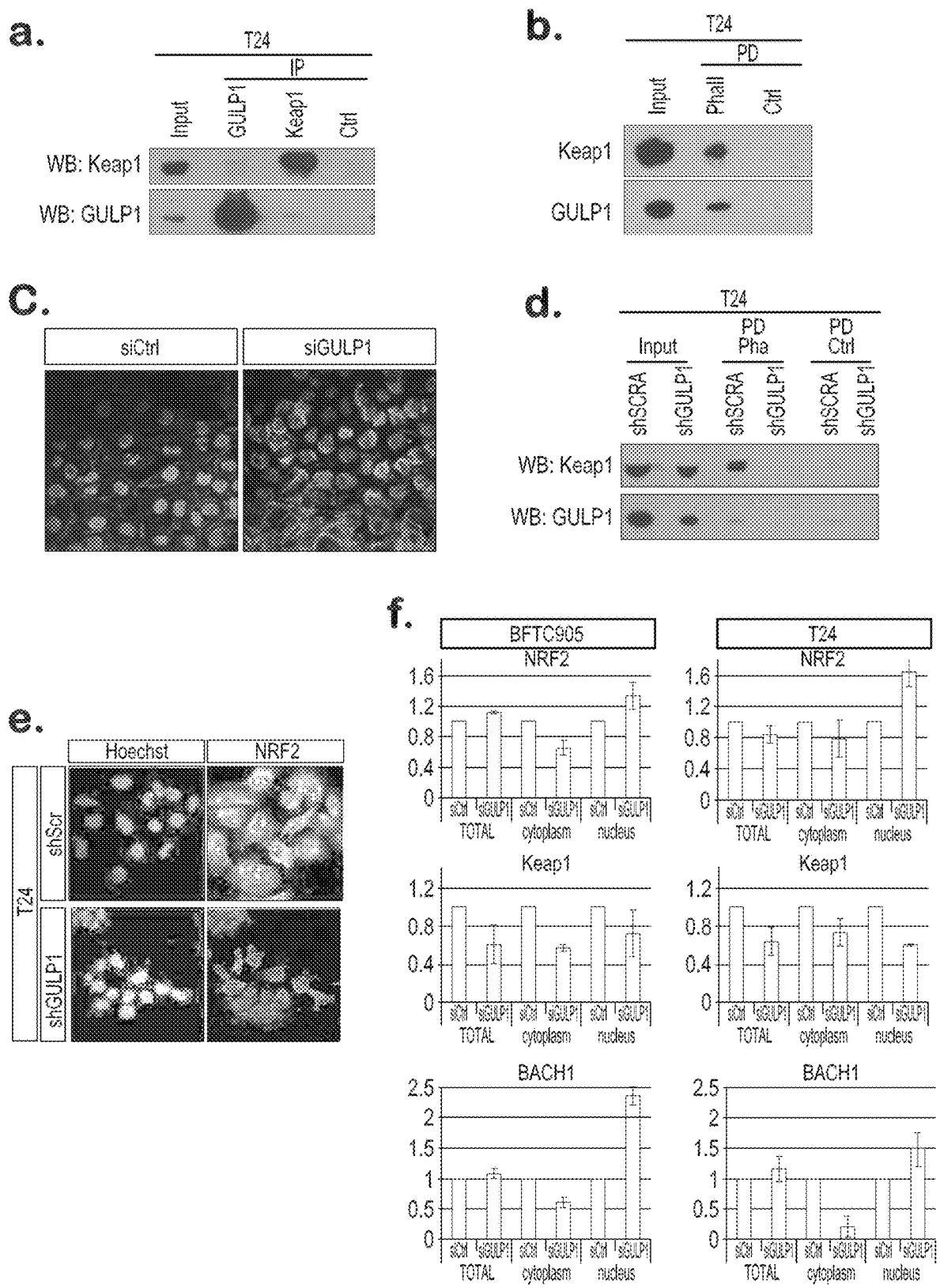
FIGS. 4*a*-4*f* are pictorial and graphical representations depicting experimental results generally relating to GULP1 down-regulation.

To understand the regulation of HMOX1 by GULP1, a possible direct interaction between GULP1 and Nrf2 and/or BACH1, the direct transcription regulators of HMOX1 was studied. To this end, co-immunoprecipitation analysis was performed of these two molecules in GULP1 highly expressed cell lines (BFTC905, BFTC909, HUC1 and T24), however, a direct protein-protein interaction between any of these proteins was not found (FIG. 8c). Therefore, upstream in the hierarchy of Nrf2 signaling pathway was focused on and a possible involvement of GULP1 in Nrf2 regulation was tested. Loss of Keap1 function leading to constitutive activation of Nrf2-mediated gene expression in cancer was previously reported; that suggests that tumor cells manipulate the Nrf2 pathway for their survival against chemotherapeutic agents. Indeed, in the basal state, Nrf2 is constantly degraded in the cytoplasm by Keap1 which anchors Nrf2 in the cytoplasm and functions as an adapter for Cul3/Rbx1 E3 ubiquitin ligase-mediated degradation of Nrf2. Since CED-6 (GULP1 homologous protein in C. elegans) and Keap1 involved in the important actin fibers rearrangements, it was hypothesized that GULP1 may interact with Keap1 for regulation of Nrf2. Interestingly, by co-immunoprecipitation experiments using T24 and BFTC905 cell lysates, it was found that GULP1 directly interacts with Keap1, the principal inhibitor of Nrf2 protein (FIG. 4a and FIG. 8d). Furthermore, pull down experiment with biotinylated-Phalloidin and the endogenous proteins GULP1 and Keap1 using cell lysates from several bladder cancer cell lines (T24, BFTC905, BFTC909) identified that each of the Keap1 and GULP1 binds directly to actin cytoskeleton (FIG. 4b and data not shown).

Having discovered GULP1 as a member of GULP1-Keap1-Actin cytoskeleton complex, whether GULP1 silencing could affect the formation and stability of actin cytoskeleton phenotype was tested. First, actin cytoskeleton staining of constitutively GULP1 silenced T24 cells and mock transfected controls with Phalloidin-Alexa488 was performed. As shown in FIG. 4c, there is a dramatic change in the cytoskeleton architecture with increasing formation of stress fibers due to silencing of GULP1, a phenotype similar to the one observed upon activation of RhoA triggered by exposure to cigarette smoking and oxidants, which very interestingly have been reported as important phenomenon causing bladder cancer transformation. More importantly, in the absence of GULP1 in T24 cells, no Keap1 signal was detected in complex with actin (FIG. 4d). These findings not only confirming the importance of GULP1 in the integrity of the actin cytoskeleton, but also underlining the crucial role of GULP1 adaptor protein in the regulation of the Nrf2-Keap1 axis.

The Tumor Suppressive Effect of GULP1 is Mediated by Influencing N112 Nuclear Activation.

Nrf2 activation is tightly regulated by a cascade of signaling events, as oxidative/electrophilic signals, that initiate a series of phosphorylation and other post-translational modification in Nrf2 itself and its negative regulators, and altogether these events activate Nrf2 leading to its nuclear accumulation. To highlight the importance of the tight regulation of Nrf2 nuclear localization, there are many reports that associate any abnormality in nuclear accumulation of Nrf2 (due to mutations or epigenetic mechanisms) with reduced apoptosis, promotion of oncogenesis and drug resistance.

Due to the key role of Nrf2 nuclear accumulation, Nrf2 immunofluorescence confocal analysis upon GULP1 ablation in two cell lines expressing endogenous GULP1 protein (T24 and BFTC905) was performed. In both cell lines, GULP1 silencing clearly induced nuclear localization of Nrf2 (FIG. 4e). This observation has been confirmed in cytoplasm-nuclear fractionation analysis in same cellular settings (FIG. 4f and FIG. 8e). Interestingly, in these sets of experiments, a decrease in Keap1 total protein levels was identified, as well as in nuclear and cytoplasmatic fractions (FIG. 4f and FIG. 8e). The exact mechanism through which GULP1 regulates Keap1 protein stability remains to be determined.

Negative Correlations Between GULP1 & Nrf2 and its Downstream Targets in a Large-Scale Analysis of Human Bladder Cancer Transcriptome.

Figures 7A, 7B, 7C, 7D:
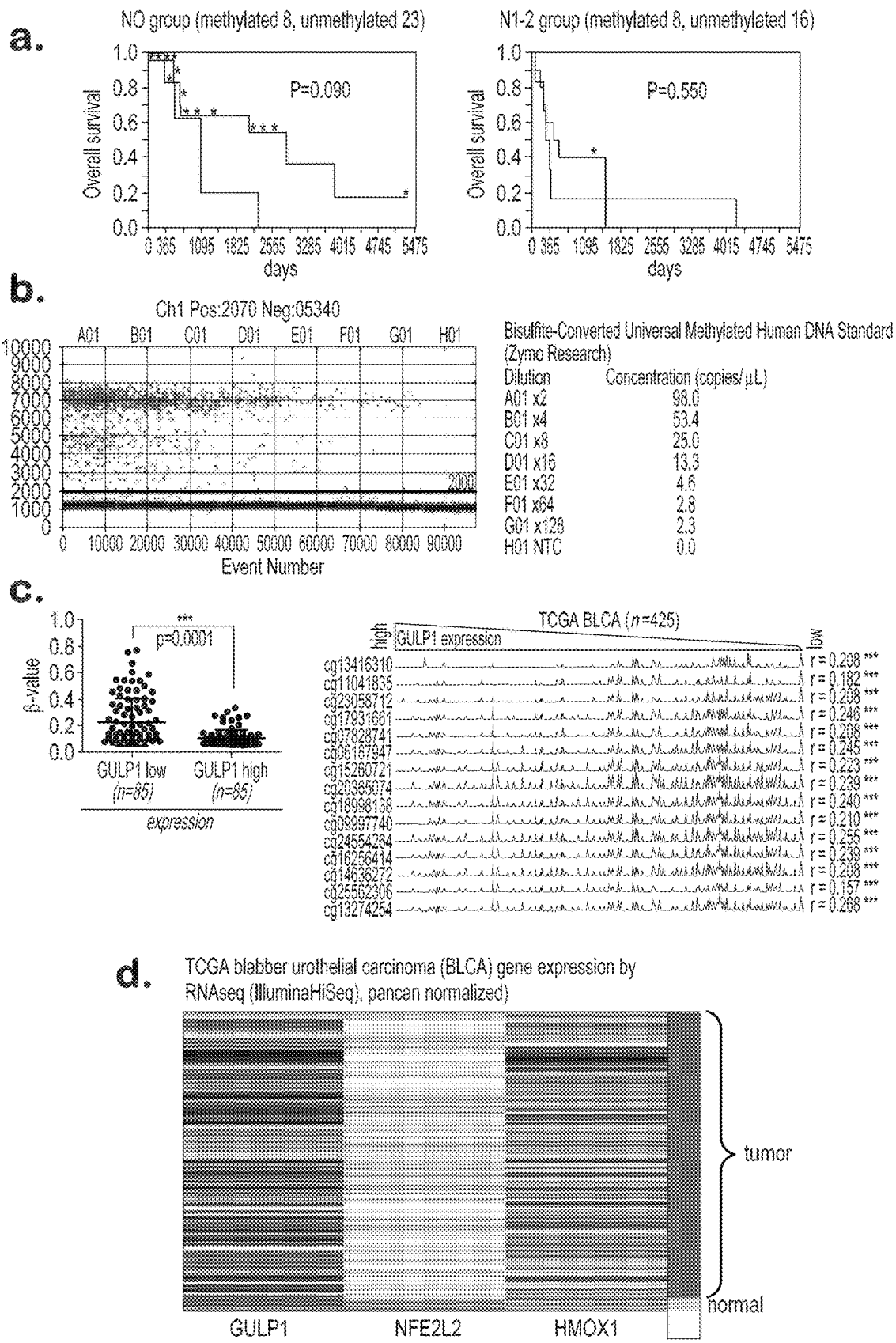
FIGS. 7*a*-7*d* are pictorial and graphical representations depicting experimental results generally relating to GULP1 down-regulation.

To verify the role of GULP1 on a large scale, we adapted a previously published array data set. GSEA was used to find gene expression signatures that correlated with GULP1 expression (FIG. 7d). Several gene sets were significant. Of them, the Nrf2 target gene set showed the strongest negative correlation with GULP1 expression. The LEF1_UP.V1_UP gene set includes the genes up-regulated in shGULP1 T24 cells. In the same data set, GULP1 down-regulation tended to be correlated negatively with Nrf2 and its down-stream target HMOX1 expression (FIG. 7d). The data set was categorized into 2 groups (low and high) based on GULP1 expression levels, and analyzed Nrf2 and HMOX1 expressions in the groups. The statistical analyses showed that Nrf2 and HMOX1 expressions inversely correlated with GULP1 expression. These findings confirmed that GULP1 regulates Nrf2 protein function and consequently the activation of its targets in the pathway.

Altogether the results suggested that GULP1 acts as a potential tumor suppressor gene that has influence on Nrf2 pathway regulation and assist Keap1 stability and its function in the cytoplasmic scaffold of Nrf2.

GULP1 Silencing Lead to Cisplatin Resistance in In Vitro and in Human Bladder Cancer Samples.

Figures 5A, 5B, 5C, 5D:
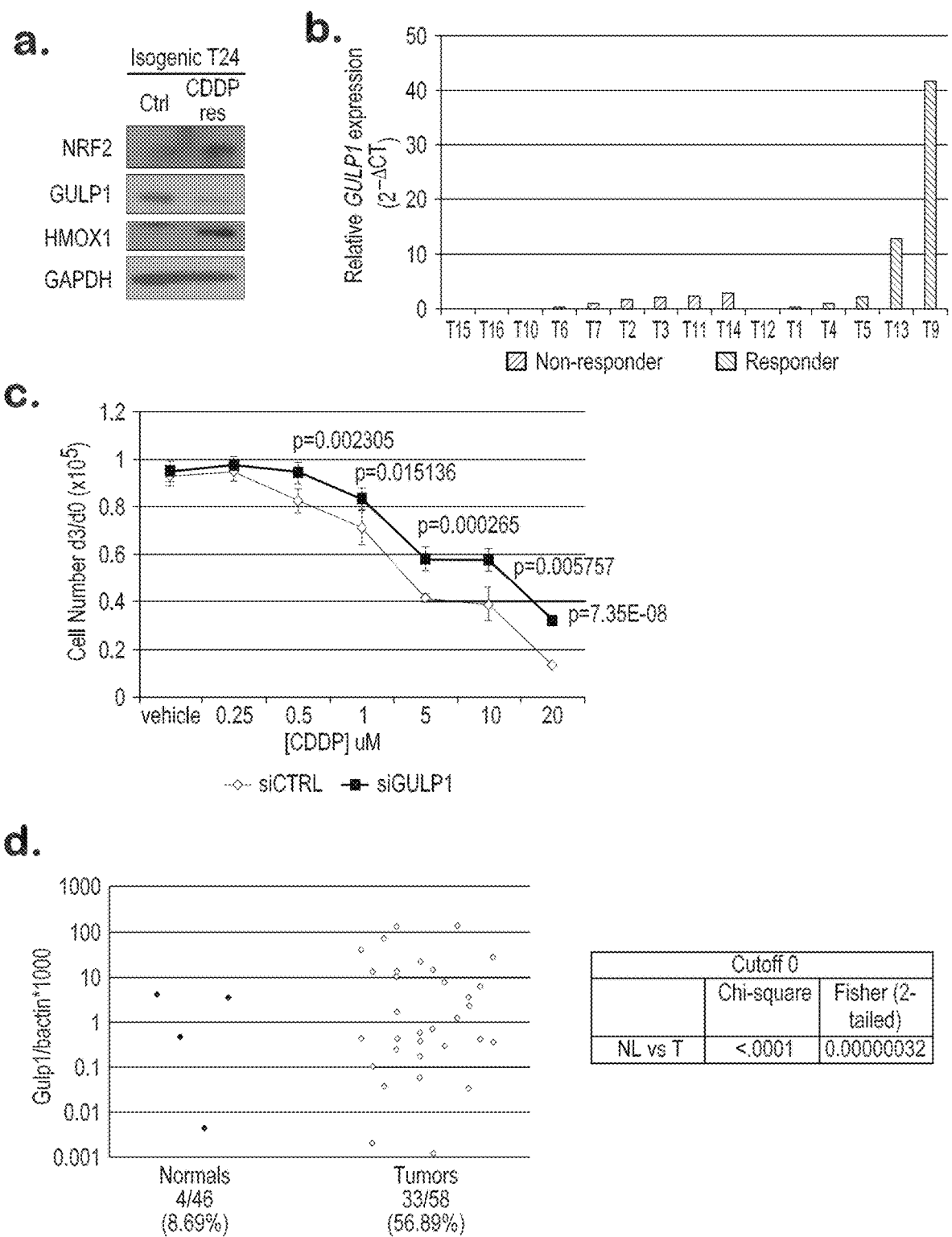
FIGS. 5*a*-5*d* are pictorial and graphical representations depicting experimental results generally relating to GULP1 down-regulation.

I was previously reported that Nrf2 mediated gene expression in cancer is associated with chemotherapeutic resistance. As the results herein support that GULP1 is a Nrf2-regulating molecule, it was hypothesized that GULP1 silencing may be associated with cisplatin resistance. To this end, two isogenic cisplatin-resistant (CDDP res) and sensitive T24 UC cell lines were tested. As expected, reduced endogenous GULP1 expression was observed in T24 CDDP resistant cells both at the transcript and protein levels in comparison with isogeneic cisplatin sensitive cells (FIG. 5a and data not shown). Furthermore, consistent with our findings above, Nrf2 and HMOX1 expression simultaneously increases in cisplatin resistant cells (FIG. 5a). To further confirm our data in in vitro, it was tested whether stable knock-down of GULP1 in T24 cells (T24 shGULP1) affect their viability after treatment with different concentration of CDDP in comparison to the control cells (T24 shScramble) (FIG. 5c). As expected, T24 shGULP1 cells had significantly higher viability than the control cells, confirming that GULP1 silencing lead to acquire CDDP resistance. To explore the human relevance of GULP1 silencing and chemotherapeutic response, we analyzed expression of GULP1 by Q-RT-PCR in a clinical cohort of UC that include 9 CDDP non-responders and 6 CDDP responders. Consistent with our cell lines data, low or no expression of GULP1 was observed in majority of cisplatin non-responders cases (FIG. 5b).

DISCUSSION

The findings discussed herein support that GULP1 expression was frequently down-regulated in bladder cancer cell lines at RNA and protein level. The subsequent immunohistochemical analysis confirmed this down-regulation in primary tumor tissue. The reduced expression of GULP1 was associated with promoter methylation as confirmed by direct bisulfate sequencing and QMSP, inferring that DNA promoter methylation is one of the main regulatory mechanism of GULP1 inactivation in UC. Reduced expression or silencing of GULP1 might abolish tumor suppression and may lead to activation of oncogenic pathway that ultimately contribute to carcinogenesis. Numerous in vitro studies were performed and different sets of primary tumor tissues were tested for promoter methylation (an epigenetic alteration which is considered to be a hallmark of cancer) to characterize GULP1 as a tumor suppressor gene (TSG). In addition, by several molecular and cell biological assay, it was determined that GULP1 is a crucial partner of a regulatory pathway for carcinogenesis. Particularly, the Nrf2-Keap1 signaling pathway was elucidated and it was found that inactivation of GULP1 lead to growth advantage (including increase proliferation and cell motility) of UC cells. Collectively, through modulating Nrf2-Keap1 signaling, GULP1 could function as a TSG by inhibiting cell growth and decreasing cellular motility.

Accumulated evidence suggest that in order to adequately manage UC, proper detection and prognostic markers are highly required in two directions. First, identification of non-invasive, low cost biomarker with high sensitivity and specificity using urine. Second, in the management of MIUC, it could be crucial the availability of a biomarker to foresee eventual chemoresistance in order to identify the best therapeutic options.

The normal human urothelium comprises a layer of basal cells that are in contact with the basement membrane, several layers of intermediate cells and a single layer of large, superficial 'umbrella' cells with a specialized apical membrane to accommodate bladder expansion and contraction.

The IHC results herein showed differential expression patterns of GULP1 in different layers of cells (Table 3). Basal part of the epithelium showed no expression, while GULP1 was expressed in luminal part. (FIG. 2b). More interestingly, the expression pattern of GULP1 in basal and liminal part are inversely correlated with promoter methylation. In several previous studies, the basal MIUCs (expressing KRT5, KRT6, KRT14, CD44 and CDH3) showed the worst prognosis, and those with papillary architecture and high expression levels of FGFR3, E-cadherin, GATA3, FOXA1 and uroplakins had the best prognosis. In this study, le to identify GULP1 silencing or methylation as a prognostic markers.

In the bladder cancer detection and diagnosis field, MSP is an ideal technique because (1) requires only small amounts of DNA, (2) as all DNA-based tests compared to RNA-based ones presents higher feasibility to be performed routinely and (3) could be done by simply using voided urine from the patients, reducing significantly the invasiveness of the test. GULP1 is expected to be an ideal target for use as a diagnostic and therapeutic marker, since significant differential expression has been evidenced between tumors and normal tissues as a consequence of epigenetic silencing. Digital droplet PCR has a possibility of increasing the detection sensitivity of GULP1 methylation. Especially in the highly diluted standard samples (×64, ×128), conventional Q-RT-PCR assay usually shows unreliable signals with high Ct values and/or inconsistency of triplicates. While, ddPCR methylation detection assay could steadily detect apparently positive signals. In this approach, a DNA sample is fractionated into more than 10,000 droplets, and PCR amplification of the template molecules occurs in each individual droplet. Using this ultrasensitive technology, very low-frequency DNA alterations, undetected in bulk sample dilutions, can be effectively identified in droplets that contain only a few copies of the alteration. Previous studies in head and neck cancers also demonstrated its excellent sensitivity of methylation detection compared with conventional Q-RT-PCR. It may exert the ability to examine samples with very small amount of DNA like urine. In this study, ddPCR assay was used for UC tissues because QMSP assay could find only 27.1% (26/96) of GULP1 methylation (FIG. 2c), while GULP1 silencing were expected to be found in 60-70% cases (75 MIUCs, 15 NMIUCs and 6 unknown) (Table S4). The ddPCR results successfully demonstrated that 60.6% (57/94, 2 N/A) of UC samples showed GULP1 methylation. Although, whether the very low level methylation has influence on its protein expression are unclear, the result implies the possibility of GULP1 methylation detection in fluid samples including urine and blood by ddPCR assay.

Obtaining a lead from RT$^2$ Profiler PCR Array Cancer PathwayFinder™ analysis, it was desired to study the association of GULP1 silencing with Nrf2-Keap axis signaling. The findings determined that silencing of GULP1 induce constitutive signaling toward Nrf2 activation and the expression of its target gene HMOX1. It was reported previously that Nrf2 activation lead to expression of numerous cytoprotective enzymes, conferring cells a survival advantage under adverse conditions in the tumorigenesis process and therapeutic resistance in many solid tumors. By in vitro analysis, GULP1 down-regulation affects Nrf2-Keap1 signaling pathway, and are inversely correlated with bladder carcinogenesis. Historically, a critical role of the Nrf2-Keap1 axis is the cytoprotection from many external and intracellular oxidative and electrophilic stresses, such as toxicants and carcinogens. However, deregulated activation of Nrf2 signaling has been more recently characterized as a deleterious switch that protect cancer cells from oxidative stress and promote their proliferation. Therefore, well control regulation of Nrf2-keap1 axis has to be considered as a critical point in the therapeutic decision making, need to protect normal cells in addition to kill tumor cells. Indeed, activation of Nrf2 signaling in more advanced stages of tumor could lead to increased expression of genes involved in drug metabolism that induce resistance to chemotherapeutic agents and radiotherapy.

Many recent reports have characterized the activation of Nrf2 pathway by various mechanisms confirming its importance during tumor progression in different cancer types. A recent study showed that increased Nrf2 protein expression in bladder cancer associated with cisplatin resistance. In lung cancer cells, Nrf2 forced activation-induced chemoresistance, whereas depletion, or Keap1 overexpression, enhanced sensitivity.

In vitro data set forth herein clearly demonstrated that Keap1 interacting molecule GULP1 is a regulatory molecules of Nrf2-Keap1 axis signaling that indicate the association of GULP1 with these proteins are related to bladder carcinogenesis and phenotypes. However, further studies using human primary tissues are needed to understand the association of GULP1-NRF2-Keap1 signaling molecules with down-stream targets such as HMOX1.

Pioneering work in C. elegans already described CED-6 (GULP1 homologous protein in C. elegans) involvement in the engulfment of apoptotic cells, a process that orchestrates important actin fibers rearrangements to permit the ruffling of the membrane at the leading edge around the cell to be phagocyted, however, role of human GULP1 during actin fibre rearrangement has not been well investigated yet. Since it has been demonstrated that Keap1 binds to actin filaments, whether the protein complex between GULP1 and Keap1 could in some way functionally be connected to the actin cytoskeleton rearrangement was investigated. Although the data suggested that GULP1 connected with actin rearrangement in association with Keap1, it is not yet known which part of the GULP1 protein particularly participates in this interaction. Further studies are needed to understand the details of synergistic biologic function of GULP1 and Keap1.

HMOX1 has been identified as a Nrf2-target gene inversely correlated with GULP1 expression in UC cell lines. Consistent with the in vitro data set forth herein, HMOX1 was reported to be overexpressed in NMIUC and MIUC. HMOX1 gene expression is up-regulated in response to oxidative stress, ultraviolet irradiation, hyperthermis, hypoxia and cytokines. In various cancers, it is also overexpressed in smokers. Above all, overexpression of HMOX1 in UCs was correlated with VEGF-D which induces tumor lymphangiogenesis, and with poor overall survival. As GULP1 inactivation (equivalent to promoter methylation) inversely associated with HMOX1 expression, it could be possible that modulating GULP1 expression may facilitate therapeutic efficacy by inhibiting HMOX1.

In patients with muscle-invasive bladder cancer (MIUC), cisplatin-based neo-adjuvant chemotherapy preceding radical surgery results in an overall long-teen survival benefit of 6%. No improvement in the survival of patients with MIUC has been accomplished over the past 20 years. As more effective targeted agents are needed for the treatment of MIUC, the use of Nrf2 inhibitors in combination with standard chemotherapeutic regimen could be applied to improve the survival outcome of bladder cancer patients. However, tight control of Nrf2 pathway is necessary in physiological conditions because Nrf2 activators represent a safe and effective strategy for the prevention of cancer and other diseases, but on the contrary, in the context of uncontrolled Nrf2 activation, such as in cancer progression, the use of Nrf2 inhibitors is needed to rescue chemosensitivity of many solid tumors. Therefore, in depth study of GULP1-Nrf2-Keap1 signaling axis may allow development of a balanced therapeutic strategy considering optimal physiologic expression of Nrf2.

UC remains to be one of the challenging disease, which has relatively high recurrence rate in early stage cases and low overall survival in advanced cases. No targeted therapies for UC are available because of small number of clinical trials performed and poor results or toxicity. It has been thought so far that this could be caused by molecular heterogeneicity of the tumors treated. In this study, GULP1 was identified as a new tumor suppressor marker of therapeutic prediction and progression. Functionally, GULP1 regulates Nrf2 pathway by assisting Keap1 stability and its function in the cytoplasmic scaffolding of Nrf2.

Figure Legends

FIG. 1 a. Expression analysis of GULP1 gene. Quantitative RT-PCR result of GULP1 for bladder cell lines was examined by $2^{-\Delta\Delta CT}$ method. Relative mRNA expression of each cancer cell line was shown (reference expression: HUC-1). Whole-cell lysates were used to detect levels of GULP1 protein and GAPDH (loading control-bottom panel). b: 5-aza-dC treatment was performed for GULP1 methylated two cell lines (HT-1376, SW780). Relative mRNA expressions (reference expression: mock sample of each cell line) were shown in bar graph. c,d: Cell proliferation ability (MTT assay) and DNA synthetic ability (BrdU assay) were analyzed using transfected bladder cancer cell lines: GULP1 has been transiently silenced in 5637 and transiently overexpressed in J82. Both cell properties have been analyzed at different time point post-transfection, indicated in the graph. Transfection efficiency of the GFP constructs (Ctrl empty and GULP-GFP) into the J82 cells have been acquired at each time point (showed in FIG. 1$d$ 72 hs post-transfection). e. Colony focus formation assay was performed in HT-1376 upon GULP1 overexpression. f. Cell migration ability of GULP1-silenced T24 cell line was compared with that of scramble sh transfected T24 cell line by wound healing assay (t0: before transfection, 24 hs: 24 hours after the transfection). Migration ratios were plotted in the bar graph.

FIG. 2 a. Immunohistochemical (IHC) analyses of GULP1 expression on 2 different UC Tissue-Micro-Arrays™ (TMA), from NMIUCs samples and the MIUCs samples. Graph represents the percentage of cases negative for GULP1 protein expression in both set of samples. The frequency of GULP1 silencing was significantly increased in the muscularis propria invaded cases rather than the lamina propria invaded cases (P<0.001, Fisher's exact test, two-tailed) or non-invasive high grade papillary cases (P<0.001). Also, the frequency was relatively decreased in the non-invasive low grade papillary cases rather than non-invasive high grade papillary cases (P=0.069). b. Representative GULP1 staining BC samples (magnification: tumor 200×, normal epithelium 400×) from the methylation analysis reported in Table 3. One representative GULP1 positive tumor and one GULP1 negative tumor along with their matched normal urotheliums are shown. As for normal tissue, GULP1 staining was focused only towards the superficial luminal aspect of the epithelium. Note the strongly positive from the surrounding muscle. c. Methylation specific PCR (QMSP) analysis of twenty pairs of UCC tumors and matched normal urothelial tissues (left) and the total cohort (right) composed of 96 tumor and 21 normal samples. Relative QMSP value was calculated as 100×QMSP (GULP1) divided by QMSP (ACTB). UCC tissues had significantly high QMSP positivity than normal tissues by empirical cut-off value (relative QMSP value=40) (left: P=0.020, right: P=0.007, both calculated by Fisher's exact test, two-tailed).

FIG. 3 a. T24 cells with GULP1 stable silenced (shGULP1) cells and T24 control cells (sh Scramble) were analyzed by RT$^2$ Profiler PCR Array Cancer PathwayFinder™ (Qiagen) to find the GULP1-related gene expression alterations. When the fold change threshold was defined as of 2 (2.0 for up and 1/2.0 for down), HMOX1 was solely extracted as a differently expressed gene (3.11 times up-regulated in T24 shGULP1 cells). b. Western blot (WB) analysis of 4 cell lines (BFTC909, T24, BFTC905 and HUC-1) upon transient GULP1 silencing. Total cell lysates have been analyzed for GULP1 and HMOX1 levels and GAPDH WB has been used as loading control. c. Left panel: WB analysis of 2 cell lines (H1376 and T24) following transient GULP1-GFP overexpression. Arrows indicate the endogenous GULP1 protein and the overexpressed GFP-tagged GULP1. Right panel: WB analysis of T24 cells upon transient GULP1 silencing (lanes 3-4) or Control siRNA transfection (lanes 1-2) and subsequent GULP1-GFP overexpression (lanes 2-4) or empty vector (lanes 1-3). Arrows indicate the endogenous GULP1 protein and the overexpressed GFP-tagged GULP1. d. Top: WB analysis of subcellular fractions of T24 cells upon GULP1 transient silencing. GULP1 protein expression was observed in both cytoplasm (central lanes) and nucleus (right lanes) of T24 cells. Inverse correlation between GULP1 and HMOX1 expression has been found both in cytoplasm and total cell lysates after inhibiting GULP1 GAPDH WB has been used as a loading control for total and cytoplasmic fractions. Bottom: Confocal imaging analysis of T24 cells in both basal condition (Ctrl—upper images) and Leptomycin B (LMB—lower images) treatment for 5 hours, to block protein export from nuclear compartment. Both GULP1 staining (red) and nuclei staining with Hoecht (blue) are shown. (images on a Nikon confocal laser scanning microscope; 63× oil-immersion objective)

FIG. 4 a. Whole-cell extracts of T24 cells were subjected to immunoprecipitation for GULP1 and Keap1 proteins, with respective antibodies previously crosslinked to ProtG™ beads, and followed by western blot analysis with the indicated antibody. An unrelated protein antibody was used as a negative control for IP and 10% of whole cell lysate was used as input. b. Actin-Pull Down of T24 cells whole-cell extracts has been performed with Biotin-conjugated Phalloidin (Phall) or no biotin-substrate (Ctrl) incubation followed by Streptavidin-beads precipitation. 10% of whole cell lysate (input) as well as precipitated fractions were analyzed by WB analysis with the indicated antibodies. c. Confocal imaging analysis of T24 cells after transient GULP1 silencing to analyze actin cytoskeleton architecture. Staining was performed with Alexa Fluor 488-conjugated Phalloidin and Hoechst nuclear stain prior to imaging on a Nikon confocal laser scanning microscope. d. Actin-Pull Down of T24 stable GULP1 silencing cells (T24 shGULP1) or control silencing clones (shSCRA), as described in FIG. 4b. e. Confocal imaging analysis of T24 stable GULP1 silencing cells (T24 shGULP1) or control silencing clones (shSCRA) upon staining with anti-Nrf2 antibody (red) and nuclei staining with Hoecsht (blue) (imaging on a Nikon confocal laser scanning microscope; 63× oil-immersion objective). f. Densitometry analysis of subcellular fractions of T24 and BFTC905 cells upon GULP1 transient silencing (siGULP1 and Control silencing-siCTRL). WB analysis images corresponding to these graphs are shown in FIG. 8e. Total, cytoplasmic and nuclear fractions for each cell line and 3 proteins (Nrf2, Keap1, Bach1) are shown, in each case values of siGULP1 are represented as relative to siCtrl values (set as 1.0).

FIG. 5 a. Western Blot analysis of the indicated proteins in T24 parental and CDDP resistant cell line. b. Clinical UC samples including 9 CDDP non-responders and 6 CDDP responders were examined by Q-RT-PCR. There were 2 cases who had relatively high GULP1 expression, and they were both CDDP responders. All non-responders showed relatively low GULP1 expression. c. T24 control and T24 stable shGULP1 cells growth curve were compared by MTT assay upon treatment with serial dilution of Cisplatin (CDDP). d. QMSP positivity of urine samples from healthy people (control) was 8.7% (4/46), and that of UCC patients was 56.9% (33/58). QMSP positive rate of urine samples from UCC patients was significantly higher than that from healthy people (P<0.001, Fisher's exact test, two-tailed).

FIG. 6 a. Direct bisulfite sequencing of GULP1 promoter region, which was the same spot of QMSP target in FIG. 2c. b. Confirmation of cell transfection efficiency for overexpression and silencing experiments in FIG. 1c, 1d, 1e. c. Cell proliferation ability and DNA synthetic ability were analyzed as in FIG. 1c, 1d using SW780 bladder cancer cell line by MTT assay and BrdU assay after 48 hour after the transfection. d. Colony focus formation assay performed as in FIG. 1e, here in T24 cells upon stable GULP1 silencing.

FIG. 7 a. Using available clinical information, overall survival of GULP/methylated cases were compared with that of GULP1 unmethylated cases according to the N stage. GULP1 methylation status caused no survival difference among lymph node metastasis positive cases. However, GULP1 methylated cases had a tendency of poor overall survival in N0 cases (P=0.090, log-rank test). b. Droplet digital PCR assay was performed using Bisulfite-Converted Universal Methylated Human DNA Standard™ (Zymo Research). Blue dots indicate droplets which include methylation positive DNA copies. As the concentration of blue dots (copies/μL) is linearly associated with the concentration of the positive standard even in the samples with very low concentration, this assay has a potential of detecting the very tiny methylated DNA copies. c. From TCGA data set, a total of 85 from each of the high and low GULP1 expressed samples were identified, and the methylation data were available for all these samples (85 high and 85 low GULP1 expressed). Low GULP1 expressed samples were highly methylated rather than high GULP1 expressed samples (P=0.0001). d. The GULP1 expression covariate was dichotomized as either high or low. To determine a threshold for GULP1 mRNA expression positivity, the distribution of GULP1 expression scores in normal versus tumor bladder tissues was compared to arrive at a cutoff threshold. As GULP1 mRNA is expressed in normal bladder tissues, a threshold such that most of all matching tumor and normal tissues had a tumor GULP1 mRNA level lower than the matching normal sample was used. This cut-off, which is equivalent to a normalized GULP1 expression score, was retained to dichotomize the GULP1 expression variable as GULP1-high or low tumors. The same procedure was performed for NFE2L2 and HMOX1

FIG. 8 a. Confocal imaging analysis of T24 cells in both basal condition (Ctrl—upper images) and Leptomycin B (LMB—lower images) treatment for 5 hours, to block protein export from nuclear compartment. Both GULP1 staining (green) and nuclei staining with Hoecsht (blue) are shown. As FIG. 3d bottom panel, but here a polylonal antibody for GULP1 staining has been used (Images acquired with Nikon confocal laser scanning microscope; 63× oil-immersion objective). b. Confocal imaging analysis of T24 cells.GULP1 staining (red) and nuclei staining with Hoecsht (blue) are shown. Different localization pattern in different cells have been indicated with yellow arrow (Cytoplasmic), green arrow (around-nuclear) and purple arrow (Nuclear) (Images acquired with E-600 microscope, 40× obj dry). c. Whole-cell extracts of T24, SV-HUC1, BFTC909, BFTC905 cells were subjected to immunoprecipitation for GULP1 with respective antibody previously crosslinked to ProtG™ beads, and followed by western blot analysis with the indicated antibodies. A not related protein antibody was used as a negative control for IP and 10% of whole cell lysate was used as input. d. Whole-cell extracts of BFTC905 cells were subjected to immunoprecipitation for GULP1 and Keap1 proteins, with respective antibodies previously crosslinked to ProtG™ beads, and followed by western blot analysis with the indicated antibodies, as shown in FIG. 4a. e. WB analysis images corresponding to the graphs in FIG. 4f. Total, cytoplasmic and nuclear fractions for each cell line (5637, BFTC905, T24) bearing medium-high levels of endogenous GULP1 are shown, analyzed with the indicated antibodies along with loading controls WB for total and cytoplasmatic fractions (GAPDH) and nuclear fraction (laminB).

Tables

TABLE 1

Primers used for RT-PCR

| Gene | Forward primer (5'-3') | Reverse primer (5'-3') | Amplicon size | Annealing temperature |
|---|---|---|---|---|
| GULP1 | TGGATGCATACACCTGAAGC (SEQ ID NO: 1) | CCTTTTGGCTGTTCCACTTC (SEQ ID NO: 2) | 124 bp | 60° C. |
| ACTB | TGGCACCACACCTTCTACAATGAGC (SEQ ID NO: 3) | GCACAGCTTCTCCTTAATGTCACGC (SEQ ID NO: 4) | 838 bp | 60° C. |

TABLE 2

Primers and Probes used for QMSP

| Gene Symbol | Forward primer (5'-3') | Reverse primer (5'-3') | Probe (5'-3') | Annealing temperature |
|---|---|---|---|---|
| *For conventional QMSP* | | | | |
| *(probe: FAM-5'-3'-TAMRA)* | | | | |
| GULP1 | TGACGTTTGTTATGGTAGCG (SEQ ID NO: 5) | TCCACGATTTCCCCACCG (SEQ ID NO: 6) | CGAGGTCGGGGACGTAGCGG (SEQ ID NO: 7) | 60.0° C. |
| ACTB | TGGTGATGGAGGAGGTTTAGTAAGT (SEQ ID NO: 8) | AACCAATAAAACCTACTCCTCCCTTAA (SEQ ID NO: 9) | ACCACCACCCAACACACAATACA (SEQ ID NO: 10) | 60.0° C. |
| *For droplet digital QMSP* | | | | |
| *(probe: FAM-5'-3'-BHQ)* | | | | |
| GULP1 | TGACGTTTGTTATGGTAGCG (SEQ ID NO: 11) | TCCACGATTTCCCCACCG (SEQ ID NO: 12) | CGAGGTCGGGGACGTAGCGG (SEQ ID NO: 13) | 60.0° C. |
| *(probe: HEX-5'-3'-BHQ)* | | | | |
| ACTB | TGGTGATGGAGGAGGTTTAGTAAGT (SEQ ID NO: 14) | AACCAATAAAACCTACTCCTCCCTTAA (SEQ ID NO: 15) | ACCACCACCCAACACACAATACA (SEQ ID NO: 16) | 60.0° C. |

TABLE 3

Association of GULP1 methylation and IHC results

| Case number | Sample ID | Site | QMSP (×1000) | GULP1 TMA results | GULP1 IHC score | Notes |
|---|---|---|---|---|---|---|
| 1 | S07-28472 | Epithelium | 0 | | 1 | Only towards lumen |
| 1 | S07-28472 | Muscle | 0 | | 3 | |
| 1 | S07-28472 | Tumor | 0 | Positive | 2 | |
| 2 | S02-29033 | Epithelium | 3054.9 | | 1 | Only towards lumen |
| 2 | S02-29033 | Muscle | 0 | | 3 | |
| 2 | S02-29033 | Tumor | 34.9 | Positive | 2 | |
| 3 | S02-61050 | Epithelium | 0 | | 1 | Very focal towards lumen |
| 3 | S02-61050 | Muscle | 393.1 | | 3 | |
| 3 | S02-61050 | Tumor | 754.5 | Negative | 0 | |
| 4 | S02-22458 | Epithelium | 0 | | 1 | Only towards lumen |
| 4 | S02-22458 | Muscle | 0 | | 3 | |
| 4 | S02-22458 | Tumor | 0 | Positive | 1 | |
| 5 | S01-11591 | Epithelium | 0 | | 1 | Only towards lumen |
| 5 | S01-11591 | Muscle | 0 | | 3 | |
| 5 | S01-11591 | Tumor | 0 | Positive | 2 | |
| 6 | S07-28276 | Epithelium | 0 | | 1 | Only towards lumen |
| 6 | S07-28276 | Muscle | 0 | | 3 | |
| 6 | S07-28276 | Tumor | 0 | Negative | 0 | |

TABLE 4

Association of GULP1 methylation with clinicopathological factors

| Factors | | GULP1 methylation tumor cohort (n = 96) | | |
|---|---|---|---|---|
| | | Unmethylated (n = 70) | Methylated (n = 26) | P value |
| Age | >60/<60 | 50/20 | 17/9 | 0.621 |
| Gender | Male/Female | 58/12 | 21/5 | 0.772 |
| Race | African-American/Others | 10/60 | 3/22 (1) | 1.000 |
| pT stage | NMIUC/MIUC | 13/52 (5) | 2/23 (1) | 0.219 |
| pN stage | Negative/Positive | 23/16 (31) | 8/8 (10) | 0.542 |
| pTNM Stage | 0, I, II/III, IV | 11/29 (30) | 2/14 (10) | 0.308 |
| Histology | UCC/SCC/Adeno | 45/9/16 | 19/4/3 | 0.464 |
| ly v invasion | Negative/Positive | 19/18 (33) | 3/11 (12) | 0.066 |

TABLE 5

Antibodies used in the study

| Target protein | Clone | Vendor | Source | Dilution used | Notes |
|---|---|---|---|---|---|
| GULP1 | Sc-374591 | Santa Cruz | Mouse | WB: 1/1000 IP: 1 µg/IP IF: 1/50 IHC: | |
| GULP1 | NBP1-84553 | Novus Biologicals | Rabbit | WB: 1/500 IF: 1/50 | |
| HMOX1 | Ab52947 | Abcam | Rabbit | WB: 1/2000 | |
| GAPDH | mAb9484 | Abcam | mouse | WB: 1/6000 | |
| ACTIN b | A2228 | SIGMA-Aldrich | mouse | WB: | |
| Keap1 | 10503-2-AP | Proteintech | Rabbit | WB: 1/4000 IP: 1 µg/IP | |
| NRF2 | D1Z9C | Cell Signaling | Rabbit | WB: 1/1000 IF: 1/50 | |
| BACH1 | Sc-14700 | Santa Cruz | goat | WB: 1/500 | |
| LAMIN B | Sc-373918 | Santa Cruz | mouse | WB: 1/2000 | |
| Goat Anti-Rabbit | Sc-2004 | Santa Cruz | goat | WB: 1/6000-10000 | HRP conjugate |
| Goat Anti-Mouse | Sc-2005 | Santa Cruz | goat | WB: 1/6000-10000 | HRP conjugate |
| Donkey Anti-goat | Sc-2020 | Santa Cruz | Donkey | WB: 1/10000 | HRP conjugate |
| Goat Anti-Mouse | A11001 | Life Technologies | goat | IF: 1/200 | Alex Fluor 488 conjugate |
| Goat Anti-Rabbit | A11011 | Life Technologies | goat | IF: 1/400 | Alexa Fluor 568 conjugate |

Materials and Methods

Cell Lines and Tissue Samples

UC cell lines 5637, HT-1376, J82, SW780, UM-UC-3, T24, Scaber, RT4 and normal human urinary tract epithelium cell line SV-HUC-1 (HUC-1) were obtained from and propagated according to the recommendations of ATCC (Manassas, Va.). BFTC-905 and BFTC-909 cell lines have been obtained from the German Collection of Microorganisms and Cell Cultures and maintained in DMEM 4.5 g/ml glucose medium. T24 and cisplatin-resistant T24 (T24 CDDP) were distributed from Kyushu university and maintained in DMEM 4.5 g/ml glucose medium. Mediums and antibiotics were purchased from Mediatech (Manassas, Va.) and supplemented with fetal bovine serum (10%) (Hyclone, Logan, Utah), 100 µg/ml streptomycin and 100 I.U./ml penicillin. Re-authentification of cells was performed using PowerPlex™ 16 HS for short tandem repeats analysis (STR) at Genetic resource core facility, the Johns Hopkins School of Medicine, Institute of Genetic Medicine and all cell lines have been confirmed as authentic. UC tissue and urine samples were obtained from Department of Urology, The Johns Hopkins University School of Medicine. Approval for research on human subjects was obtained from The Johns Hopkins University Institutional Review Boards. This study qualified for exemption under the U.S. Department of Health and Human Services policy for protection of human subjects [45 CFR 46.101(b)].

DNA and RNA Extraction

Cell pellets were digested with 1 SDS and 50 µg/ml proteinase K (Roche, Nutley, N.J.) at 48° C. overnight. Isolation of genomic DNA from cell lines was performed with the phenol-chloroform extraction protocol followed by ethanol precipitation as previously described. Bladder tissue samples were digested with 1% SDS and 50 µg/ml proteinase K at 48° C. for 2 days. DNA from tissue was extracted with phenol by using MaXtract™ High Density tubes (Qiagen, Valencia, Calif.). For RNA extraction, adherent cells were detached and followed by the procedure of the PureLink™ RNA Mini kit (Life Technologies, Carlsbad, Calif.). RNA extraction from bladder tissue was performed with the QIAzol™ Lysis Reagent (Qiagen) following manufacturer's protocol.

5-Aza-2'-Deoxycytidine (5-Aza-dC) Treatment of Cell Lines

Twenty four hours before treatment, cells were plated at low density (1-3×10⁶ cells, dependent on growth characteristics of the respective cell line) in T75 cm² Tissue Culture Flasks (BD Biosciences, Bedford, Mass., USA). Stock solutions of 100 mM 5-Aza-dC (Sigma-Aldrich, St. Louis, Mo.) and 5 mM Trichostatin A (TSA) (Sigma-Aldrich) were prepared with DMSO (Sigma-Aldrich). Immediately before addition to the cell culture medium, appropriate aliquots of the stock solutions were dissolved in PBS (pH 7.5). Cells were treated with 5 µM 5-Aza-dC for 3 to 5 days. Medium with 5-Aza-dC was changed daily. Additionally, combination treatment with 5-Aza-dC and TSA was performed by adding 5 µM of 5-Aza-dC daily for 5 days and TSA (300 nmol/L) was added to the medium for the final 24 hours. Cells were harvested 24 hours after the last day of treatment (5-Aza-dC only and 5-Aza-dC+TSA) for RNA extraction and the analysis of gene expression by Reverse Transcriptase-PCR (RT-PCR).

Reverse Transcription-PCR (RT-PCR) and Quantitative Reverse Transcription Real Time PCR (Q-RT-PCR)

Total RNA (500 ng) from cell lines and from bladder tissue were reverse-transcribed with qScript cDNA SuperMix™ (Quanta BioSciences) kit. The primers were designed by using Primer3 software. Primer sequences and annealing temperatures were shown in Table 1. Actin type B (ACTB) was used as a loading control. The reactions were carried out with primers, SYBR Green PCR Master Mix™ (Life technologies) in triplicate using 7900HT real time PCR machine (Life technologies). PCR conditions were 1 cycle: 95° C. for 10 min; followed by 40 cycles: 95° C. for 15 s and 60° C. for 60 s. Expression of the gene of interest was quantified by $2^{-\Delta\Delta C_T}$ method.

Bisulfite Treatment and Sequencing

Bisulfite conversion of 1 ug gDNA was performed by EpiTect™ Bisulfite kit (Qiagen) following the manufacture's protocol, and amplified by forward and reverse primers which were designed in the promoter CpG islands of GULP1 gene. PCR products were purified using the QIAquick™ Gel Extraction kit (Qiagen), and sequenced by Genewiz DNA sequencing service (Genewiz, South Plainfield, N.J.).

Methylation-Specific PCR (MSP) and Quantitative MSP (QMSP)

Primers were designed using the MethPrimer™ algorithm and MSP primer algorithm. ACTB was served as a reference gene. QMSP primers and probes for GULP1 and ACTB were provided in Table 2. Serial dilutions (30-0.003 ng) of Bisulfite-Converted Universal Methylated Human DNA Standard™ (Zymo research, Irvine, Calif.) were used as a positive control to construct a standard curve for each plate. Amplification reactions were carried out in triplicate in a final volume of 10 µl containing 1.5 µl bisulfite-modified DNA, 600 nmol/l forward and reverse primers, 200 nmol/l probe, 0.6 unit Platinum Taq DNA Polymerase (Invitrogen), dATP, dCTP, dGTP, and dTTP in a concentration of 200 µmol/l each, respectively, and 6.7 mmol/l $MgCl_2$. Amplification reactions were carried out in 384-well plates in a 7900HT Fast Real-Time PCR System™ (Life technologies) and were analyzed by the Sequence Detector System™ software (SDS 2.4 software, Applied Biosystems). The relative level of methylated DNA for each gene in each sample was determined as a ratio of QMSP value of the amplified gene to β-actin, multiplied by 1000 for easier tabulation.

Droplet Digital PCR (ddPCR)

Bisulfite treated DNA samples (2 ul) were added to ddPCR assay mixture (18 ul) including ddPCR Supermix™ with probes (no dUTP) (Bio-rad Laboratories, Hercules, Calif.). Primers and probes of target genes and reference gene (ACTB) are available in Table 1. Each of the ddPCR assay mixture (20 ul each) were loaded into each sample well of the droplet generator cartridge (total eight cartridge) (Bio-rad Laboratories). Additionally 70 µl of droplet generation oil (Bio-rad Laboratories) was loaded into each of the droplet generator cartridge. The QX200™ droplet generator (Bio-rad Laboratories) created an average of 20,000 oil droplets per sample in each well and clouded droplet samples were transferred to a 96-well PCR plate (Eppendorf, Hauppauge, N.Y.). The plate was heat-sealed with foil and placed into a thermal cycler under the following conditions: 95° C. for 10 minutes, then 40 cycles of 95° C. for 30 seconds and 60° C. for 1 minute and two final steps at 98° C. for 10 minutes and 4° C. hold to enhance dye stabilization. Finally, the plate was placed on the QX200™ droplet reader (Bio-rad Laboratories). The results were analyzed by QuantaSoft™ software (Bio-rad Laboratories). All samples were analyzed in duplicate, and ACTB un-amplified samples were excluded. The average positive droplet counts of duplicate samples was used for analysis. In effect, a sample was classified as positive if either of the duplicates showed a positive droplets.

Cell Proliferation Assay (MTT Assay and BrdU Incorporation Assay)

Bladder cancer cell lines HT-1376, SW780 and 5637 were plated on a 96-well plate at a density of $1 \times 10^4$ per well and incubated overnight at 37° C. The next day, cells were transfected with GULP1 expression vector (pCMV6-AC-GULP1-GFP) or empty vector (pCMV6-AC-GFP) (Origene, Rockville, Md.) and X-tremeGENE9™ transfection reagent (Roche) for overexpression. GULP1 small interfering RNA (siRNA) (Silencer Select™ GULP1—ID: s28162) or control siRNA (Silencer Select™ Negative Control No. 1 siRNA) (Life technologies) and RNAiMAX™ transfection reagent (Life technologies) were transfected to 5637 cells for inhibition. Cellular viability was measured by the 3-(4, 5-dimethyl thiazol-2-yl)-2,5-diphenyl tetrazolium bromide (MTT) proliferation assay kit (ATCC, Manassas, Va.) according to the manufacturer's instructions after different time points. At the end of each time point, 10 µl of MTT labeling reagent (5 mg/ml MTT) was added to the culture medium, which was then incubated in the dark for a further 4 h at 37° C. This step was followed by cell lysis with the addition of 100 µl of a SDS-based detergent reagent. The plates were incubated for 2 h at 37° C. to dissolve formazan crystals. Spectrophotometric readings (570 nm-650 nm) were obtained on a Spectra Max™ 250 96-well plate reader (Molecular devices, Sunnyvale, Calif.). Each assay was performed in triplicate, and each experiment was repeated at least three times. Data are represented as the extent of cellular survival expressed as a ratio to 24 hour time point value for each group. To measure DNA synthesis, cell proliferation was also performed with the BrdU cell proliferation enzyme-linked immunosorbent assay kit (Roche). Briefly, Transfected cells in 96 well plates were labeled for 2 h with BrdU at 24, 48 and 72 h after seeding. BrdU incorporated into cellular DNA was quantified as instructed by the manufacturer.

Colony Formation Assay

Colony focus formation assays were performed as described previously. Using GULP1 expression vector (pCMV6-AC-GULP1-GFP), empty vector (pCMV6-AC-GFP) (Origene, Rockville, Md.) and X-tremeGENE9™ transfection reagent (Roche), HT-1376 bladder cancer cell lines were transfected with the GULP1 overexpression or empty vector construct. For GULP1 inhibition, lentivirus particles (pGFP-C-shLenti, TL304167, Origene), scramble vector (pGFP-C-shLenti, TR30021, Origene), shRNA lentiviral packing kit (TR30022, Origene) and authenticated 293T cell (ATCC, Manassas, Va.) were used following the manufacture's protocol. Forty eight hours after transfection, cells were divided into 3 dishes for each of the construct and drug treatment were started in the following day (G418 treatment (250 ug/ml) for pCMV6-AC-GFP vector and puromycin (0.25 ug/ml) for pGFP-C-shLenti vector). To confirm the expression of GULP1 in transfected cells, one additional dish of transfected cells were cultured for 48 hours, RNA was extracted and GULP1 expression was confirmed by quantitative reverse transcription-PCR (Q-RT-PCR). After 2 weeks of drug treatment, cells were washed twice with PBS, fixed with 25% acetic acid and 75% methanol at room temperature for 10 minutes and then stained with 0.1% crystal violet. Colonies (>2 mm in diameter) were counted and the number of colonies per dish was averaged from three independent experiments.

Cancer PathwayFinder™

In order to find GULP1-related pathway, we used $RT^2$ Profiler PCR Array Cancer PathwayFinder™ (Qiagen) and 7900HT real time PCR machine (Life technologies) following the manufacture's instruction. Scrambled RNA transfected T24 cell was used as a control, and shRNA-GULP1 transfected T24 cell as a test sample. Transfection was performed by lentivirus particles as described in the colony formation assay section. Xx hours after transfection cell were harvested and RNA was extracted by using standard protocols. After PCR, the results were analyzed by $RT^2$ Profiler PCR Array Data Analysis™ software v3.5. ACTB was used as a reference gene.

Western Blot

Protein lysates were prepared as described previously or as detailed in every experimental analysis. Total protein were transferred to a nitrocellulose membrane (BioRad) after separation on 4-12% Bis Tris precast gel (BioRad, Hercules, Calif.) or 10-20% tris Glycine precast gel. The blots were blocked with Phosphate Buffer Saline, 0.02% Tween and 5% milk (BIORAD) and incubated with specific antibodies for each gene at 4° C. overnight. Antibodies used in this study are described in Table 5. After washings, individual blot was incubated with their respective secondary antibody (Cell Signaling Technology, Danvers, Mass.) and the signal was detected with enhanced chemiluminescence reagents (Amersham, Pittsburgh, Pa.) according to the manufacture's protocol. Densitometry analysis was performed by using ImageJ™ programme.

Immunoprecipitation and Phalloidin Pull Down

Lysis of cells was performed in CoIP buffer (150 mM NaCl, 50 mM Tris pH7.5, 0.5% NP40, 10% glycerol, 1 mM EDTA) supplemented with phosphatase inhibitors (PhosphoSTOP, Roche) and protease inhibitors (EDTA-free Complete, Roche). After preclearing with magnetic Protein G beads (BIORAD) for 2 hours at 4° C., lysates were then incubated overnight with the indicated antibody, previously covalently bound to magnetic Protein G beads using 5 mg/ml dimethylpimelimidate (Pierce). Immunoprecipitated proteins were separated by SDS-PAGE and analyzed by Western Blot with the indicated antibodies according to standard procedures.

For in vitro Pull down binding assays, cells were harvested in lysis buffer (as previously) and protein concentration was determined by a BCA Protein Assay Kit™ (Pierce, 23225), ~1 mg of lysate incubated with Phalloidin-biotin conjugated (SIGMA) at final concentration of 5 µM for 6 hours at 4° C. and then streptavidin-coated magnetic beads (Cell Signaling Technology) were added for 30 minutes. Streptavidin purified protein complexes, as well as 1% (5 µg) of total extract, were resolved by SDS-PAGE analysed by Western Blot with the indicated antibodies according to standard procedures.

Immunohistochemical Staining (IHC) and Tissue Microarray (TMA)

Immunohistochemical analysis for GULP1 was performed on 10 micron tissue/cell lines slides after a step of antigen retrieval in microwave oven for 20 min in Tris-HCl+ EDTA (pH 9.0), at 750 W. Slides were then incubated overnight at 48° C. (1.5 mg/ml concentration of primary antibody). Hydrogen peroxide, serum biotinylated immunoglobulins, and avidin-biotin complexes were used according to the manufacturer's instructions (Dako, Golstrup, Denmark). After induction of the color reaction with freshly made diaminobenzidine solution (Dako), slides were counterstained with hematoxylin. TMA slides consists of 104 single-punches of 0.6 mm in diameter were also stained by the same procedure. The GULP1 staining intensity was evaluated by a senior pathologist.

Immunofluorescence Analysis

Cells were grown on glass coverslips for 72 hs. After fixation in 4% paraformaldehyde, they were incubated in PBS 0.2% Glycine, permeabilized with PBS 10% Triton X100 for 10 minutes and incubated in Blocking buffer (PBS 3% BSA, 10% goat serum, 0.02% Tween) for 2-3 hours at r.t.

Incubation with the indicated primary antibodies (see Table 5) has been performed at 4° C. in the dark. After 5 washing with PBS 0.02% Tween, coverslips have been incubated with the indicated secondary antibodies (Table 5) for 1 h at r.t. For the case actin cytoskeleton analysis, after fixation, the coverslips have been incubated 90 minutes with Alexa Fluor® 488 Phalloidin (Life Technologies, 1:1000 in PBS). Nuclei were counterstained with 4',6-diamino-2-phenylindole (DAPI) contained in the mounting media Prolong Antifade™ reagent (Thermofisher). Slides were examined and photographed using a fluorescence microscope.

Nuclear-Cytoplasmic Fractionation

Nuclear and cytoplasmatic protein lysate were prepared from UC or HUC1 cells using the Nuclear/Cytosol Fractionation™ Kit (Biovision, K266-25) according to the manufacturer's instructions. Briefly, cultured cells were washed with PBS and treated with cytosol extraction buffer on ice. After centrifugation, supernatant was used as cytoplasmic protein fraction and the nuclear pellet was incubated with nuclear extraction reagent, vortexed 30 seconds followed by 10 minutes incubation on ice, for 4 repetitions. The protein concentrations of each extract were measured with the BCA Protein Assay Kit™ (Pierce, 23225) and after dilution with ×4 sample buffer containing beta-mercaptoethanol, the samples were heat-denatured at 100° C. for 10 min. Equal amounts of each sub-cellular fraction were loaded on 4-12% Tris-Glycine pre-cast gels (Life Technologies, EC61385) and analyzed by Western Blotting with the indicated antibodies.

Statistical Analysis

Continuous variables were analyzed by Student's t-test, two tailed, and categorical variables were analyzed by Fisher's exact test. Survival outcome was analyzed by log-rank test. All statistical analyses were performed using JMP 9™ software (SAS institute, Cary, N.C., USA). The level of statistical significance was set at $P<0.05$.

Although the invention has been described with reference to the above example, it will be understood that modifications and variations are encompassed within the spirit and scope of the invention. Accordingly, the invention is limited only by the following claims.

---

What is claimed is:

1. A method for detecting a urothelial cell proliferative disorder associated with engulfment adaptor PTB domain containing 1 (GULP1) in a subject comprising:
   a) contacting a target deoxyribonucleic acid (DNA) in a sample of urothelial tissue or biological fluid from the subject containing urothelial cells with a reagent which detects methylation of the promoter region of GULP1, wherein the reagent is (i) a probe comprising SEQ ID NO:7 or (ii) at least one GULP1 oligonucleotide primer comprising SEQ ID NO:6; and
   b) detecting methylation of the promoter region of GULP1 DNA, wherein hypermethylation of the promoter region of GULP1 DNA relative to a control is indicative of a urothelial cell proliferative disorder.

2. The method of claim 1, wherein the subject is a mammalian subject.

3. The method of claim 1, wherein the biological fluid is selected from the group consisting of a biopsy specimen, a tissue specimen, ejaculate, urine and blood.

4. The method of claim 1, wherein the probe is detectably labeled.

5. The method of claim 4, wherein the label is selected from the group consisting of a radioisotope, a bioluminescent compound, a chemiluminescent compound, a fluorescent compound, a metal chelate, and an enzyme.

6. The method of claim 1, wherein the cell is an epithelial cell.

7. The method of claim 1, wherein the cell proliferative disorder is carcinoma of the bladder, ureters, kidney, or renal pelvis.

8. The method of claim 1, wherein the at least one GULP1 oligonucleotide primer further comprises SEQ ID NO: 5.

9. The method of claim 1, wherein the contacting step comprises contacting DNA in the sample with an agent that modifies nonmethylated cytosine residues, amplifying CpG-containing nucleic acids by means of CpG-specific oligonucleotide primers, wherein the oligonucleotide primers distinguish between modified methylated and nonmethylated nucleic acid, and wherein the oligonucleotide primers comprise at least one GULP1 oligonucleotide primer comprising SEQ ID NO:6, and the detecting step comprises detecting the methylated CpG-containing promoter region based on the presence or absence of amplification products produced in the amplifying step.

10. The method of claim 9, wherein the at least one GULP1 oligonucleotide primer further comprises SEQ ID NO: 5.

11. The method of claim 9, wherein the amplifying step comprises a polymerase chain reaction.

12. The method of claim 9, wherein the modifying agent is bisulfite.

13. The method of claim 9, wherein cytosine is modified to uracil.

14. A method for monitoring the effectiveness of a therapeutic regimen in a subject having a urothelial cell proliferative disorder associated GULP1 comprising:
   a) contacting a target deoxyribonucleic acid (DNA) in a sample of urothelial tissue or biological fluid from the subject containing urothelial cells with a reagent which detects methylation of the promoter region of GULP1, wherein the reagent is (i) a probe comprising SEQ ID NO:7 or (ii) at least one GULP1 oligonucleotide primer comprising SEQ ID NO:6, wherein the contacting of the sample occurs simultaneously with and/or following a course of treatment; and
   b) detecting the level of methylation of the promoter region of GULP1 DNA, wherein a reduction of methylation of the promoter region of GULP1 DNA as compared to methylation of the promoter region of GULP1 DNA from the subject prior to the therapeutic regimen is indicative of effectiveness of a therapeutic regimen for treatment of urothelial cell proliferative disorder in the subject.

15. The method of claim 14, wherein the therapeutic regimen is chemotherapy.

16. The method of claim 15, wherein the chemotherapy is paclitaxel or cisplatin.

17. A method for providing a prognosis to a subject having a urothelial cell proliferative disorder associated GULP1 comprising:
   a) contacting a target deoxyribonucleic acid (DNA) in a sample of urothelial tissue or biological fluid from the subject containing urothelial cells with a reagent which detects methylation of the promoter region of GULP1, wherein the reagent is (i) a probe comprising SEQ ID NO:7 or (ii) at least one GULP1 oligonucleotide primer comprising SEQ ID NO:6, wherein the contacting of the sample occurs simultaneously with and/or following a course of treatment;
   b) detecting the level of methylation of the promoter region of GULP1 DNA; and
   c) providing a prognosis to the subject based on (b), wherein a reduction of methylation of the promoter region of GULP1 DNA as compared to methylation of the promoter region of GULP1 DNA from the subject prior to treatment is indicative of an increase likelihood of cancer-free survival in the subject.

18. The method of claim 17, wherein the subject is undergoing a therapeutic regimen.

19. The method of claim 18, wherein the therapeutic regimen is chemotherapy.

20. The method of claim 19, wherein the chemotherapy is paclitaxel or cisplatin.

21. The method of claim 14, wherein the at least one GULP1 olignucleotide primer further comprises SEQ ID NO: 5.

22. The method of claim 11, wherein the at least one GULP1 olignucleotide primer further comprises SEQ ID NO: 5.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens
<220> FEATURE:
<221> NAME/KEY: misc_feature
<223> OTHER INFORMATION: Primer used for RT-PCR

<400> SEQUENCE: 1
tggatgcata cacctgaagc                                              20

```
<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: Primer used for RT-PCR

<400> SEQUENCE: 2 cctttttggct gttccacttc                                              20

<210> SEQ ID NO 3
<211> LENGTH: 25
<212> TYPE: DNA
<213> ORGANISM: Homo sapiens
<220> FEATURE:
<221> NAME/KEY: misc_feature
<223> OTHER INFORMATION: Primer used for RT-PCR

<400> SEQUENCE: 3
tggcaccaca ccttctacaa tgagc                                         25

<210> SEQ ID NO 4
<211> LENGTH: 25
<212> TYPE: DNA
<213> ORGANISM: Homo sapiens
<220> FEATURE:
<221> NAME/KEY: misc_feature
<223> OTHER INFORMATION: Primer used for RT-PCR

<400> SEQUENCE: 4
gcacagcttc tccttaatgt cacgc                                         25

<210> SEQ ID NO 5
<211> LENGTH: 20
<212> TYPE: DNA
<213> ORGANISM: Homo sapiens
<220> FEATURE:
<221> NAME/KEY: misc_feature
<223> OTHER INFORMATION: For conventional QMSP

<400> SEQUENCE: 5
tgacgtttgt tatggtagcg                                               20

<210> SEQ ID NO 6
<211> LENGTH: 18
<212> TYPE: DNA
<213> ORGANISM: Homo sapiens
<220> FEATURE:
<221> NAME/KEY: misc_feature
<223> OTHER INFORMATION: For conventional QMSP

<400> SEQUENCE: 6
tccacgattt ccccaccg                                                 18

<210> SEQ ID NO 7
<211> LENGTH: 20
<212> TYPE: DNA
<213> ORGANISM: Homo sapiens
<220> FEATURE:
<221> NAME/KEY: misc_feature
<223> OTHER INFORMATION: For conventional QMSP (probe: FAM-5'-3'-TAMRA)

<400> SEQUENCE: 7
cgaggtcggg gacgtagcgg                                               20

<210> SEQ ID NO 8
```

```
<211> LENGTH: 25
<212> TYPE: DNA
<213> ORGANISM: Homo sapiens
<220> FEATURE:
<221> NAME/KEY: misc_feature
<223> OTHER INFORMATION: For conventional QMSP

<400> SEQUENCE: 8
tggtgatgga ggaggtttag taagt                                          25

<210> SEQ ID NO 9
<211> LENGTH: 27
<212> TYPE: DNA
<213> ORGANISM: Homo sapiens
<220> FEATURE:
<221> NAME/KEY: misc_feature
<223> OTHER INFORMATION: For conventional QMSP

<400> SEQUENCE: 9
aaccaataaa acctactcct cccttaa                                        27

<210> SEQ ID NO 10
<211> LENGTH: 30
<212> TYPE: DNA
<213> ORGANISM: Homo sapiens
<220> FEATURE:
<221> NAME/KEY: misc_feature
<223> OTHER INFORMATION: For conventional QMSP (probe: FAM-5'-3'-TAMRA)

<400> SEQUENCE: 10
accaccaccc aacacacaat aacaaacaca                                     30

<210> SEQ ID NO 11
<211> LENGTH: 20
<212> TYPE: DNA
<213> ORGANISM: Homo sapiens
<220> FEATURE:
<221> NAME/KEY: misc_feature
<223> OTHER INFORMATION: For droplet digital QMSP

<400> SEQUENCE: 11
tgacgtttgt tatggtagcg                                                20

<210> SEQ ID NO 12
<211> LENGTH: 18
<212> TYPE: DNA
<213> ORGANISM: Homo sapiens
<220> FEATURE:
<221> NAME/KEY: misc_feature
<223> OTHER INFORMATION: For droplet digital QMSP

<400> SEQUENCE: 12
tccacgattt ccccaccg                                                  18

<210> SEQ ID NO 13
<211> LENGTH: 20
<212> TYPE: DNA
<213> ORGANISM: Homo sapiens

<400> SEQUENCE: 13
cgaggtcggg gacgtagcgg                                                20

<210> SEQ ID NO 14
<211> LENGTH: 25
<212> TYPE: DNA
<213> ORGANISM: Homo sapiens
<220> FEATURE:
```

```
<221> NAME/KEY: misc_feature
<223> OTHER INFORMATION: For droplet digital QMSP

<400> SEQUENCE: 14
tggtgatgga ggaggtttag taagt                                          25

<210> SEQ ID NO 15
<211> LENGTH: 27
<212> TYPE: DNA
<213> ORGANISM: Homo sapiens
<220> FEATURE:
<221> NAME/KEY: misc_feature
<223> OTHER INFORMATION: For droplet digital QMSP

<400> SEQUENCE: 15
aaccaataaa acctactcct cccttaa                                        27

<210> SEQ ID NO 16
<211> LENGTH: 30
<212> TYPE: DNA
<213> ORGANISM: Homo sapiens
<220> FEATURE:
<221> NAME/KEY: misc_feature
<223> OTHER INFORMATION: For droplet digital QMSP (probe: HEX-5'-3'-BHQ)

<400> SEQUENCE: 16
accaccaccc aacacacaat aacaaacaca                                     30
```